United States Patent
Gurin

(10) Patent No.: US 11,529,434 B1
(45) Date of Patent: Dec. 20, 2022

(54) DYNAMIC RECONFIGURABLE CONTAMINATION REDUCTION CONTROL SYSTEM

(71) Applicant: Michael Gurin, Glenview, IL (US)

(72) Inventor: Michael Gurin, Glenview, IL (US)

(73) Assignee: Michael Gurin, Glenview, IL (US)

( * ) Notice: Subject to any disclaimer, the term of this patent is extended or adjusted under 35 U.S.C. 154(b) by 440 days.

(21) Appl. No.: 16/839,082

(22) Filed: Apr. 3, 2020

Related U.S. Application Data

(63) Continuation-in-part of application No. 16/546,089, filed on Aug. 20, 2019, now abandoned.

(51) Int. Cl.
| | |
|---|---|
| *A61L 2/232* | (2006.01) |
| *A61L 2/24* | (2006.01) |
| *G05B 19/042* | (2006.01) |
| *G16H 70/60* | (2018.01) |

(52) U.S. Cl.
CPC .............. *A61L 2/232* (2013.01); *A61L 2/24* (2013.01); *G05B 19/042* (2013.01); *G16H 70/60* (2018.01); *A61L 2202/14* (2013.01); *G05B 2219/25252* (2013.01)

(58) Field of Classification Search
CPC ........ A61L 2/24; A61L 2/232; A61L 2202/14; G16H 70/60; G05B 19/042
See application file for complete search history.

(56) References Cited

U.S. PATENT DOCUMENTS

| | | | |
|---|---|---|---|
| 8,431,910 B1* | 4/2013 | Perry | A61L 2/10 250/455.11 |
| 2021/0000991 A1* | 1/2021 | Kraus | A61L 2/24 |

* cited by examiner

*Primary Examiner* — Sean E Conley

(57) ABSTRACT

A control system and pathogen inactivation method to reduce cross-contamination within operational devices that experience sequential touching of touch spots on the operational device by multiple people. Additionally, the system controls and then executes the reconfiguration of touch spot position to increase the probabilistic time interval between sequential touches from a first person to a second person physically interacting with the operational device. The dynamic reconfiguration control system reduces the probability of cross-contamination between sequential personal touches in sequential user sessions.

20 Claims, 8 Drawing Sheets

Fig. 1
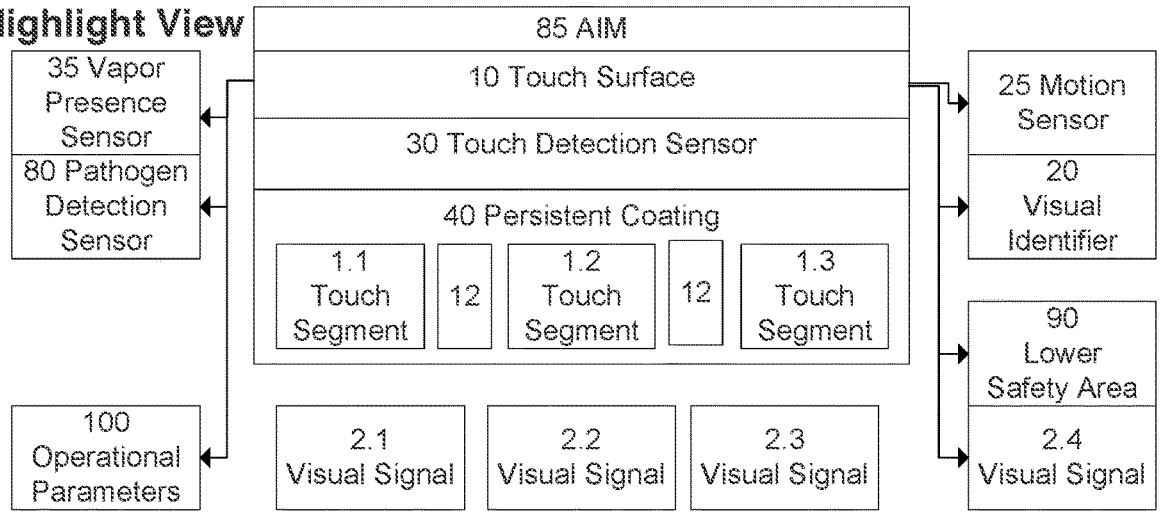
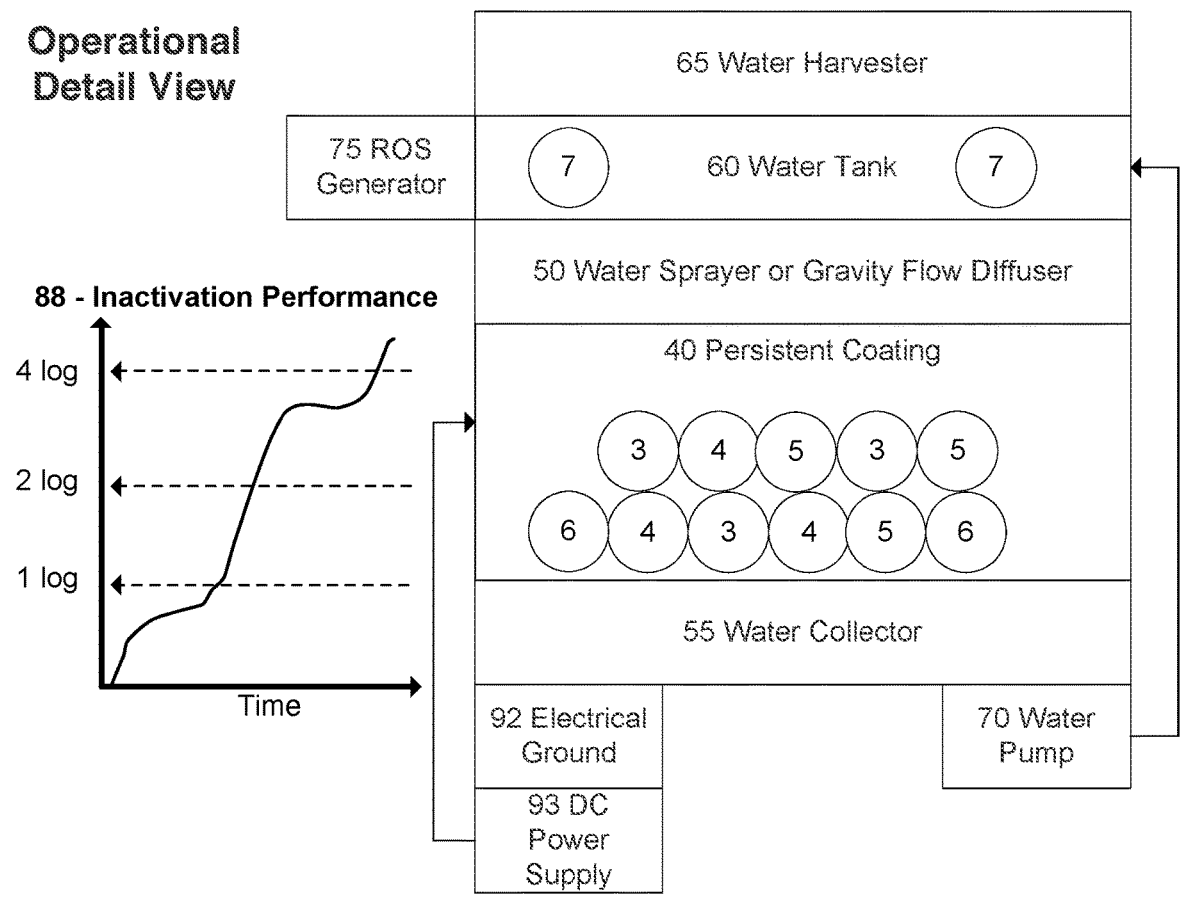

Fig. 2

Operational Highlight View top view

| 110.1 Actuator ||
|---|---|
| 120.1 Position | 120.2 Position |
| 85 AIM | |

| 10 Touch Surface | | |
|---|---|---|
| 1.1 Touch Segment | 140.1 Shield | 1.2 Touch Segment |
| 110.2 Actuator || |
| 140.2 Shield | | |

131 Passerby

130 User

Fig. 3 side view

| 2.11 Visual Signal | 2.21 Visual Signal | 2.31 Visual Signal |
|---|---|---|
| 85 AIM |||

| 41 Air/Water Interface | | |
|---|---|---|
| 40 Persistent Coating ||| 
| 30 Touch Detection Sensor |||
| 1.1 Touch Segment | 1.2 Touch Segment | 1.3 Touch Segment |
| 2.1 Visual Signal | 2.2 Visual Signal | 2.3 Visual Signal |

Individual touches = A1 ... An
A = duration of touch
B = duration between touches
Other parameters = average duraction of touch, average duration between touches, mean duration between touches

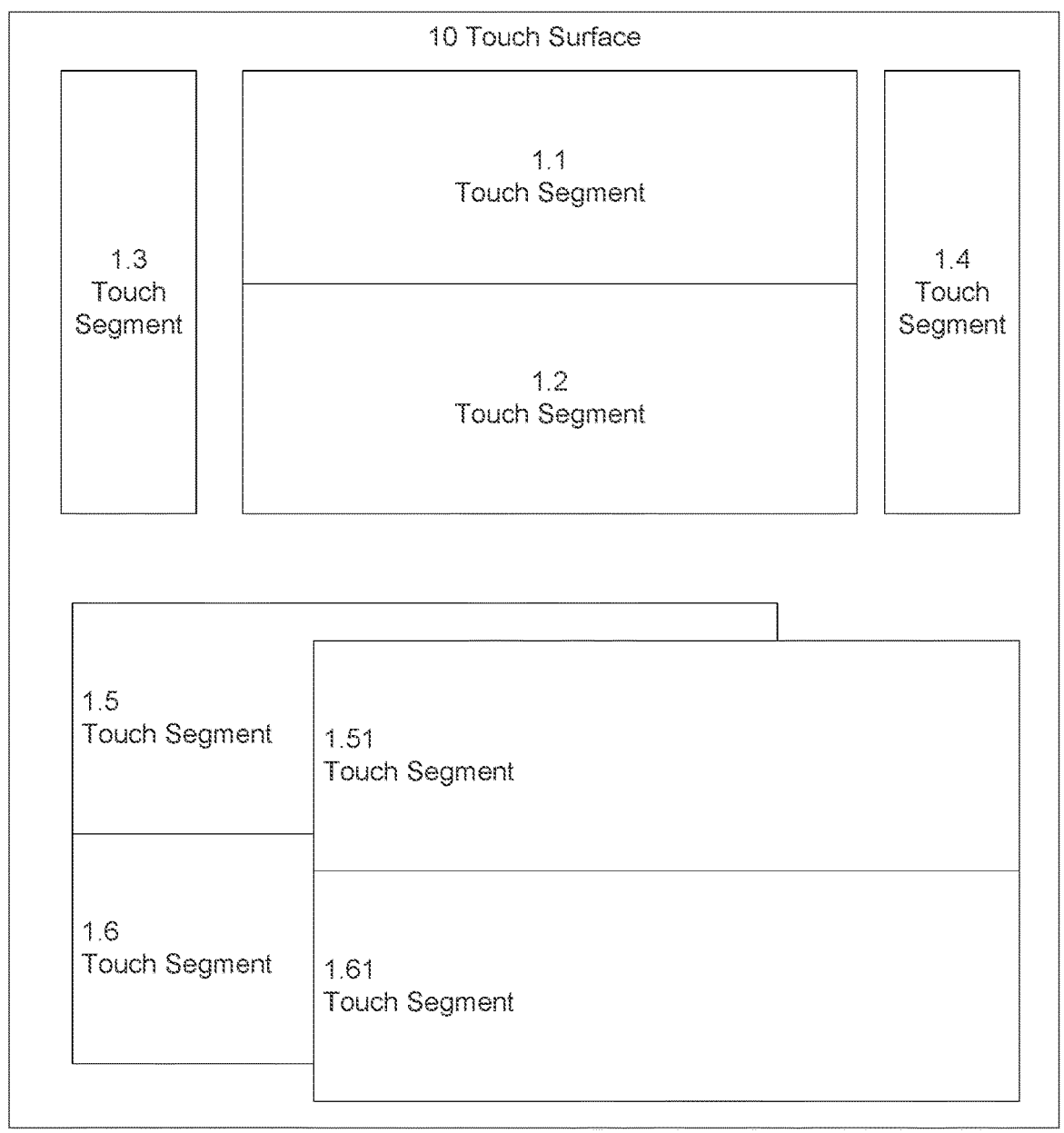

DYNAMIC RECONFIGURABLE CONTAMINATION REDUCTION CONTROL SYSTEM

This patent document contains material subject to copyright protection. The copyright owner, also the inventor, has no objection to the reproduction of this patent document or any related materials, as they appear in the files of the Patent and Trademark Office of the United States or any other country, but otherwise reserves all rights whatsoever.

CROSS-REFERENCE TO RELATED APPLICATIONS

This application claims the benefit of patent application U.S. Ser. No. 16/546,089 filed on Aug. 20, 2019 titled "Infectious Disease Feedforward and Feedback Control with Integral Theranostics System", and hereby incorporated by reference in their entirety.

FIELD OF INVENTION

The present invention relates to decontamination hardware electronics equipment operable to reduce cross-contamination that are specifically operated in accordance to parameters that are touch-specific including through the coordination, reconfiguration and visual feedback control system to overcome lagging response times of disinfectant liquids and/or persistent antimicrobial/antifungal/antiviral coatings (collectively hereinafter referred to as pathogens and therefore the coating being a "Mysophobic coating") in which surface pathogens are inactivated. The control system has suitability in a wide range of exemplary operational devices ranging from door handles and knobs, water dispensers including sinks, water fountains, kiosks, touchscreens, keypads including the entry of personal identification numbers (a.k.a. PIN), escalators, elevator buttons, hand rails including rails within mobile vehicles that transport people, security screening bins, beverage serving pitchers, tables, condiment dispensers, food serving utensils, etc. to decrease decontamination effectiveness.

BACKGROUND OF INVENTION

Prior art for decontamination of pathogens on high-frequency with fast-interval touch points in public places are extremely limited in reducing cross-contamination probability approaching zero. Traditional disinfectants are known to meet the threshold of relatively quickly inactivating pathogens, though even fast-acting disinfectants such as Clorox® require the disinfectant solution to be in contact for five minutes. Categorically this means that any subsequent touch requires five minutes to provide an adequate level of protection. Even worst, any subsequent and sequential touch point after a complete disinfection process has no long-term persistence and therefore subjects the touched surface with any pathogens being carried by that subsequent touch and thereafter prior to that subjects touching of the same surface. Therefore, the yet subsequent sequential touch point is not at all protected by the earlier disinfection process at time zero by any touches that take place after time zero until such time as the subject's current touch.

Additional prior art for decontamination also includes so-called persistent coatings in which an embedded active to inactivate pathogens (or a subset of potential pathogens) has ongoing inactivation though not instant. Common persistent coatings such as provided by Microban® or HygraTek® respectively have complete inactivation times that are respectively on the order of 2 hours or more, and on the order as low as 2-3 minutes. Though the HygraTek coating is much faster acting it is clear that subsequent sequential touches having an interval of less than 2-3 minutes will not substantially eliminate cross-contamination from all of the recent prior touch points (however it will be substantially reduce the probability of cross-contamination due to the pathogen viability window being reduced from 2 hours to less than 2-3 minutes. Clearly in both instances' persistence is a valuable method in reducing the probability of cross-contamination within the threshold period of complete inactivation time, but it clearly doesn't approach a zero probability against cross-contamination.

A need exists to minimize cross-contamination rate due to sequential physical touching on a substrate post disinfectant application and prior to sufficient time duration of persistent decontaminating completion, including the objective of maximizing decontamination confidence particularly to germophobes. This is of particular importance as highlighted by the recent coronavirus Covid-19 global pandemic.

SUMMARY OF INVENTION

The present invention is a dynamic reconfiguration control system "DRS", also referred to as dynamic cross-contamination reduction control system, having the ability to operate as a standalone device into a range of operational devices that have physical interaction with potential sources of pathogens that adhere to operational device, yet the optimal system further contains integral and networked devices to extend the functionality including adjusting to specific pathogens of concern (e.g., Covid-19) and personalized based on past prior or future physical interactions.

The fundamental object of the invention is to minimize subsequent physical touches by a second person on a same touch spot (also referred to as a touch segment) that as the prior first person touch spot such by either reconfiguring the user interface to reduce the probability of touching on that same touch spot or to have a visual signal indicating a safer second touch spot to substantially reduce cross-contamination probability.

Another object of the invention is to provide visual indication (visual signal or changing of graphical user interface for a touch panel) of the safest second touch spot on an operational device having at least one of a persistent anti-pathogen (preferably being a mysophobic coating such that the persistent coating is at least effective against two of antimicrobial, antiviral, and antifungal) coating or active pathogen inactivation method to maximize the time interval between the last touch by the first person (i.e., first user session) and the subsequent first touch by the second person (i.e., second user session).

Yet another object of the invention is to contain or shield the first touch spot prior to pathogen inactivation so as to not contaminate a second person touching that same first touch spot.

Another object of the invention is such that the containment or shielding of the first touch spot increases the effectiveness of an active pathogen inactivation method.

Yet another object of the invention is that the containment or shielding of the first touch spot protects the second person during the active pathogen inactivation method on the first touch spot.

A further object of the invention is that the containment or shield of the first touch spot increases the concentration of non-thermal plasma over the first touch spot by reducing the distance between the containment or shield and the surface of the first touch spot.

Yet another object of the invention is that the containment or shield of the first touch spot increases the concentration of microwave energy over the first touch spot by reducing the distance between the containment or shield and the surface of the first touch spot while protecting the second person during the microwave energy generation to inactivate any pathogens on the first touch spot.

Yet another object of the invention is to increase the production of reactive oxygen species "ROS" incorporating a catalyst within a coating on the first touch spot.

Another object of the invention is to provide increased confidence to a germophobe (a.k.a. mysophobia) by actively showing a touch spot that is safer for touching than another touch spot.

Yet another object of the invention is to provide increased confidence to a germophobe (or just a curious person) by actively engaging with the control system so as to experience a higher level of control/empowerment through interacting with the control system and therefore a higher level of confidence in the legitimacy of the visual signals/indicators.

Another object of the invention is to provide visual feedback to the subsequent person prior to a touch event that accurately reflects the safety from cross-contamination as a function of time interval since the most recent touch event, and preferably a visual heat-map showing relative safety within the various physical space in which a subsequent touch event can take place.

Yet another object of the invention is to use an active pathogen inactivation method to reduce adhesion between a touch surface and transfer of any potential pathogens on the part of the body of the second person to that touch surface.

Another object of the invention is to increase surface water on the touch surface, preferably as adsorbed water, to increase the effectiveness of the active pathogen inactivation method.

Yet another object of the invention is to increase the reactive oxygen species "ROS" solubilized in surface water to further increase the effectiveness of an active pathogen inactivation method.

Another object of the invention is to accelerate the rate of pathogen inactivation by combining a surface upwards towards air/water-interface and an air/water-interface downwards to surface beyond each of the individual methods.

An object of the invention is to reduce the cross-contamination of sequential touches by at least 5%, or at least 50% through active visual signaling and/or active inactivation methods.

All of the aforementioned features of the invention fundamentally recognize the dynamic reconfiguration and/or guided behavior modification to reduce cross-contamination on touch surfaces beyond the presence of any passive anti-pathogen coating on the touch surface.

BRIEF DESCRIPTION OF DRAWINGS

FIG. 1 is an operational view at the component level depicting both a highlight and a detail view of the AIM system.

FIG. 2 is a top view at the component level for a multi-position actuated system.

FIG. 3 is a side view of the AIM system depicting alternative approaches of embedded or projected visual signals.

FIG. 12 is a top view depicting a graphical user interface having dynamic reconfiguration within a multi-segmented touch screen

DEFINITIONS

Figure 4:
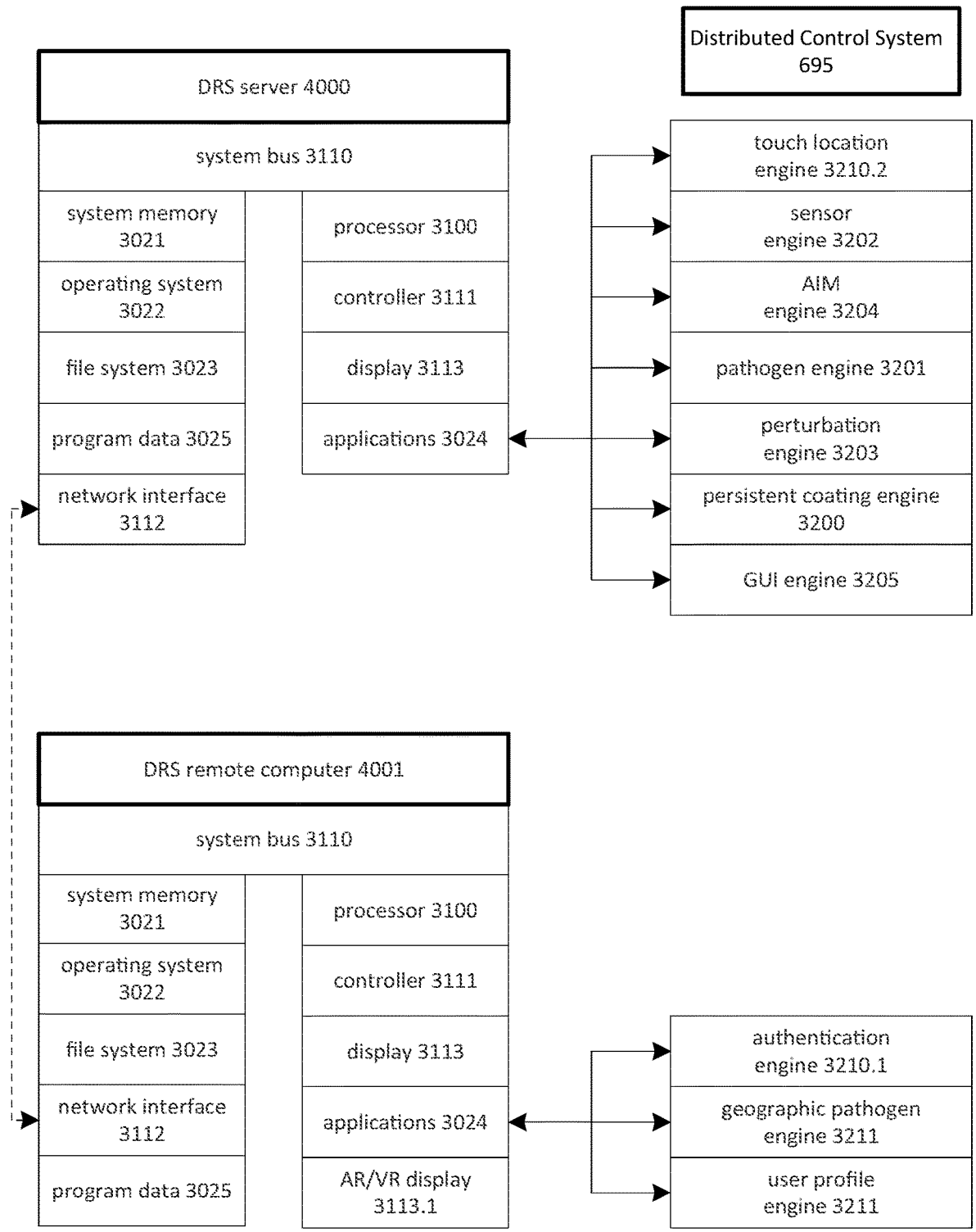
FIG. 4 is component level architecture of the control system including remote and distributed control components.

The term "operational device" includes devices in which people physically interact by directly touching at least one surface area on the operation device. The range of operational devices include, whether in public or private physical spaces, door handles and knobs, water dispensers including sinks, water fountains, kiosks, touchscreens, keypads including the entry of personal identification numbers (a.k.a. PIN), escalators, elevator buttons, hand rails including rails within mobile vehicles that transport people, security screening bins, beverage serving pitchers, tables, condiment dispensers, food serving utensils, steering wheels or joysticks, buttons including buttons on a casino slot machine, seats on transport vehicles, etc.

The term "cross-contamination" is the act of transferring contaminants, notably of concern are infectious pathogens (hereinafter referred to as "pathogens"), from either person to person directly or as directly relevant in this invention from person (first) to touch spot to person (second).

The term "switching time-interval" is the duration of time between a last touch by a first person to the first touch by a subsequent second person on the same touch spot. More precisely it is the time period between the end of the first person's user session on the operational device until the beginning of the second persons user session on that same operational device. Generally a time-interval is the time period between two events and in the context of this invention it is the time-interval (also used interchangeably as time interval) between a last touch event on an operational device touch surface by a first person and a second touch event on that same operational device touch surface by a subsequent second person.

The term "adhesion" is the act of transferring contaminants, again of notable concern are pathogens, from person to surface and therefore having the potential for subsequent transfer from surface to a subsequent person. The term "surface-adhesion" refers to the adhesion of pathogens resulting from a person (first) physically touching a surface. The term "adhesion-transference" refers to the touch surface (of operational device) to subsequent persons (second, third, etc.) touching that same touch spot.

The term "reactive oxygen species" is also referred to as "ROS". It is understood that the broader reference to ROS is also understood to be the broader generation of free-radical.

The term "motion sensor" is a sensor in the broadest sense of the word (and as known in the art can include infrared arrays, camera, etc.) is a hardware device capable of detecting movement or the presence of a person (or any living object including pets). The preferred motion sensor has the ability to determine when a first person leaves an operational device and when a second person arrives (or is anticipated to arrive) that same operational device. Therefore, the ability to distinguish between a first person interacting with the operational device and a second person interacting with that same operational device is achieved. It is understood that the DRS controller in combination with the motion sensor calculates the actual time in which the first person leaves the operational device, the running interim time since the last touch event of the first person, and the time (including projected time) in which the second person arrives at the operational device.

The term "interim time", used interchangeably with "running interim time" is that actual real-time between the time in which the last touch event on the operational device touch surface occurred. It is understood that each touch segment of the operational device touch surface, in the preferred embodiment, has a distinct running interim time.

The term "persistent coating" is a functional top (upper-most relative to the air/water interface) coating of the substrate, having an pathogen inactivation activity time of greater than 1 hour, preferably greater than 1 day, particularly greater than 1 week, and specifically greater than 1 month, concurrently with a pathogen inactivation time to reach 1 log reduction of less than 2 hours, preferably less than 10 minutes, particularly lower than 3 minutes, and specifically lower than 1 minute or even as low as lower than 10 seconds (it is understood that the persistent coating also has pathogen inactivation times to reach 2 log (and preferably the ability to reach a 4 log reduction and therefore a corresponding pathogen inactivation time to reach that 4 log reduction).

The term "active pathogen inactivation method", or also hereinafter referred to as "AIM", is the use of an active method (i.e., not passive notably in comparison to a static persistent coating void of any external energy, externally emitted energy (whether it is optical, magnetic, electrical, electrostatic, etc.) to inactivate pathogens that reside on a touch surface.

DETAILED DESCRIPTION OF INVENTION

Here, as well as elsewhere in the specification and claims, individual numerical values and/or individual range limits can be combined to form non-disclosed ranges.

Exemplary embodiments of the present invention are provided, which reference the contained figures. Such embodiments are merely exemplary in nature. Regarding the figures, like reference numerals refer to like parts.

The invention significantly reduces the cross-contamination of contagious pathogens through sequential physical touch interactions on the same operational device. It is recognized that physically touching a surface has the ability to transfer contaminants including harmful pathogens from one person (first person) to another subsequent (second person, third person, etc.) that physically interacts with an operational device by touching the same spot. It is further recognized that even operational devices having embedded actives on the touch spot, such as silver ions, copper ions, as well as other antiviral, antifungal, or antimicrobial actives, fail to inactivate pathogens remaining on the touch spot due to surface-adhesion prior to the time-interval between subsequent touches. To be clear, a silver ion-based solution that typically takes in excess of 2 hours to inactivate pathogens on a surface due to surface-adhesion has essentially no efficacy in a scenario having a time-interval of less than 20 minutes let alone less than 5 minutes. One such instance is the time-interval between passengers at an airline kiosk. Another such instance is the time-interval between door handles at a quick-serve restaurant that is often less than 2 minutes. Another instance is the time-interval at a salad bar for serving utensils in a self-serve salad bar which is often less than 15 seconds. In the instance of the salad bar (i.e., any serving utensil whether it be used for cafeteria, desert bar, etc.) it is understood that each food item is equivalent to an aggregate touch surface comprised of at least two serving utensils (the first serving utensil is equivalent to the operational device first touch segment, and the second serving utensil is equivalent to the operational device second touch segment). Alternatively, the serving utensil can have a handle sufficiently large to segment into at least two segments. Yet another alternative, though not preferred, is for the serving utensil to be dedicated to a single food item and there to be only one serving utensil for that single food item, where the DRS has an embedded visual indicator that switches from a safe to at least a less safe status as a function of running time interval and the pathogen inactivation method having a log reduction rate that is also a function of running time interval.

This failure in efficacy is precisely the fundamental purpose of this invention such that dynamic reconfiguration and/or visual referencing of prior touch spots increases the time-interval between actual sequential touch spots and therefore providing more time for any persistence coating or active method to reduce the potential for subsequent cross-contamination. The fundamental objective is to minimize immediately subsequent physical touches by a second person on the same touch spot by dynamically changing the user-interface such that a second touch spot, different than the first touch spot as the prior first person, is subsequentially touched to substantially reduce the cross-contamination probability. Multiple methods are controlled by the DRS to increase the probability (or even certainty) of the second touch spot being different than the first touch spot. The first method centers around the reconfiguration of a graphical user interface. It is understood that a typical graphical user interface having a touchscreen/display or a dynamic display screen that may be without a touchscreen though having fixed buttons (typically at the bottom) of the display screen based on suggested hot buttons at the perimeter of the touchscreen. Contrary to the typical graphical user interface, the inventive DRS uses at least a heat-map of immediately prior touch spots to alter the subsequent second person/user of the operational device graphical user interface by varying the placement of touch spots by at least a half inch displacement. The preferred embodiment uses a probability overlaid heat-map (i.e., a touch surface area 2-dimensional mapping of actual touch spots including an overlay of actual touch times in which each touch takes place, notably as a database, and an overlay of probability within the touch surface area 2-dimensional mapping for each segment of a projected user session) such that touch spots touched at the ending portion of the first person's user session are substantially out of commission for the second person's user session (or at least substantially reduced probability in the beginning portion).

The beginning portion is defined as the first 50% of a projected second session, preferably as the first 25% of a projected second session, or particularly preferred to be a projected period of time the interval between touching a first touch spot by the first person and the touching of that same spot by the second person greater than a 1 log reduction of cross-contamination, preferably greater than a 2 log reduction of cross-contamination, and particularly preferred greater than a 4 log reduction of cross-contamination. Therefore the DRS is comprised of a heat-map for the entire touch-surface in at least a 2-dimensional mapping space, a separate heatmap is provided for each segmentation of the projected user session time (preferably the segmentation is at least two segments being the beginning portion and the ending portion, particularly preferred segmentation by at least time intervals equivalent or less than the 1-log reduction of cross-contamination time though more preferred by at least time intervals of the 0.2 log reduction of cross-contamination time). Each heat-map also has a probability value in the two-dimensional space for each segmentation of a projected user session. The DRS utilizes the multiple segmented heat-maps and their respective probability overlays such that placement of candidate touch spots at the beginning portions of a second person minimize the likelihood of touching a same spot at the ending portions of the first person. An alternative approach is such that candidate touch spots within the actual ending portions of the first person are entirely void from candidate touch spots within the projected beginning portions of the second person. Yet another alternative approach is such that candidate touch spots within the entire first person's user session are entirely void from candidate touch spots within the entire second person user session. The DRS can simply offset the displacement of touch spots position between user sessions by at least half an inch, preferably by at least one inch, or offset entire portions of the user interface by graphical segments within the touch surface area by at least two inches recognizing that a user may accidentally touch a non-candidate touch spot of the touchscreen leading to cross-contamination as well. When the DRS is also comprised of at least one active pathogen inactivation method, yet another alternative is such that placement of candidate touch spots in the beginning segments of a second user to be void of a space in which the at least one active inactivation method is acting on (i.e., a mechanical movement of the at least one active pathogen inactivation method moves over the touch surface areas that were contaminated in the prior first person session). This enables an increased amount of time for the active pathogen inactivation method to reduce the potential for cross-contamination. One exemplary active pathogen inactivation method includes the application (or spraying) of known disinfectants in the art. Another exemplary active pathogen inactivation method includes the creation of ROS, whether by non-thermal plasma, ion generators, microwave, or ultra-violet LEDs as known in the art. Regardless of the method used the inventive DRS reduces the probability by at least 50%, preferably by at least 80%, and particularly preferred by at least 95% a sequential touch interval time by making the projected time interval for any sequential touch spots greater than at least a 0.2 log reduction time (and preferably at least a 1.0 log reduction, and particularly preferred at least a 2.0 log reduction, and superior preference at least a 4.0 log reduction. This critical time interval is a function of pathogen, in which the DRS can take a probability representation on a pathogen susceptibility index where the pathogen susceptibility index varies on a seasonal basis, based on a geographic outbreak incidence, or even customized to a second persons personal susceptibility index on a pathogen basis.

Turning to FIG. 1, FIG. 1 has two views: an operational highlight view and an operational detail view with the latter providing additional details of components within the operational highlight view. This embodiment has an AIM 85 that has an emitted energy field in communication with the touch surface 10, that as shown is an integral component of the touch surface 10 (e.g., an optical waveguide of light such that a portion of the light is emitted into the persistent coating 40. It is understood that the AIM 85 doesn't have to be in physical communication with the touch surface 10 with an exemplary instance being an array of ultraviolet-C emitting LEDS that project optically onto the touch surface 10. The touch surface 10, as depicted here has an integral touch detection sensor 30 (e.g., traditional touch screens as known in the art) that communicates to a DRS controller each instance of a touch event by a user of the operational device (collectively the components in which the touch surface has a persistent coating is on or in which the AIM projects its energy field onto the touch surface). The touch detection sensor 30, though depicted as being in physical communication with the touch surface 10 and the persistent coating 40, can utilize a motion sensor 25 to determine where a user touches and therefore the DRS calculates which touch segment 1.1 (first position), 1.2 (second position), or 1.3 (third position) and the corresponding time in which that user touch took place. It is understood that the touch surface 10 can consist of only one touch segment but this exemplary use case requires the presence of an AIM 85 to provide pathogen inactivation. Each touch segment 1.1, 1.2, and 1.3 has an individual corresponding visual signal 2.1, 2.2, and 2.3 in which the DRS calculates as a function of time an at least relative safety to touch one touch segment as opposed to another having the lowest probability of pathogen cross-contamination between subsequent touches on the touch surface 10 by a first person to a second person. The visual signals 2.1, 2.2 and 2.3 as shown are projecting an optical light onto the corresponding touch segment, though it is understood that the visual signals can be in physical, as well as optical, communications with the touch segment or through the persistent coating when the persistent coating 40 is at least optically translucent (or optically clear). Additional details on the motion sensor 25, operational parameters 100 in which the DRS utilizes as inputs and calculated parameters to determine precise control of outputs including and notably visual signals 2.1, 2.2, and 2.3 in addition to outputs to the AIM 85. The DRS system, in its preferred embodiment, also has a visual identifier 20 utilized to provide authentication of DRS activity and performance of routine maintenance events on the DRS within the identified operational device such that the DSR maintains records of activity and maintenance either locally or remotely. Another preferred feature is a lower safety area 90 that is particularly relevant to germophobes (as detailed further within this specification). The lower safety area 90 also has a visual signal 2.4 such that the user has a clear and distinct visual indication that this area 90 has the lowest safety, at least relative to the touch segments 1.1, 1.2, and 1.3. The particularly preferred embodiment also has a vapor presence sensor 35 and/or a pathogen detection sensor 80 respectively to validate the inactivation performance of the persistent coating and AIM 85 on the touch surface (when void of a persistent coating) or first on the persistent coating 40 being the outermost layer (i.e., closest to the air/water interface) with the touch surface 10 being the host substrate. The visual signal 2.4 of the lower safety area, understanding that the lower safety area can be also a touch segment that has been more recently had a touch interaction, but it also can be an area outside of the touch surface and therefore void of any touch segments. The preferred embodiment of the lower safety area 90 has its associated visual signal 2.4 that pulses on and off, and the visual signal color has a visual wavelength higher than 565 nm (and preferably higher than 625 nm). The particularly preferred embodiment has the pulsing begin when the second person (or even first person) is approaching the operational device (when the motion sensor 25 indicates the presence of a next user). A specifically preferred embodiment has the pulsing frequency vary by at least 10% (and preferably by at least 50%) amplifying to the next user that the controller 3111 is working (as opposed to a regular blinking light that is more readily tuned into the subconscious). The embodiments that utilize thermal inactivation as the AIM 85 process further includes a thermal isolation barrier 12 between the individual touch segments (1.1, 1.2, and 1.3). The preferred thermal isolation barrier 12 reduces heat transfer between the respective touch segments by at least 10% in the in-plane direction (and preferably by at least 50%, and particularly preferred by at least 80%). It is further understood that the AIM 85 can include segmented (though not shown) emitting fields such that only one touch segment receives the emitted energy field at a time (or at least the safest touch segment i.e., the touch segment to be used by the second person is either shielded from or void of emitted energy source from AIM 85).

The utilization of pulsing visual signals in the preferred embodiment, whether they be associated with the touch segments or the lower safety area, also serves the role of saving energy particularly of interest when the operational device is battery or wireless power enabled. The visual signal on-time duration, relative to the off-time duration, of the touch segment having the highest running time interval increases as the second person approaches (as provided by the motion detection sensor 25 such that the preferred motion sensor has at least two motion sensitive areas to differentiate between a first person using the operational device and a second person that is/will be approaching the operational device). The visual signal on-time duration, relative to the off-time duration, of the touch segment having the lowest running time interval decreases as the second person approaches (again as provided by the motion detection sensor 25). The ratio of on-time duration to off-time duration preferably starts from greater or equal to 1:10 (when no second person is present) to greater or equal to 2:1 (when a second person becomes present). The particularly preferred embodiment also has the visual signal of the touch segment having the highest running time interval (i.e., the safest surface to touch, the touch surface touched by the first person the longest time ago) with a lower wavelength (preferably less than 565 nm) than the visual signal of the touch segment having the shortest running time interval (i.e., the least safe surface to touch, the touch surface touched by the first person most recently). The preferred embodiment has the lower wavelength differential being at least 30 nm, and particularly preferred at least 50 nm, with the specifically preferred visual signal for safest touch surface being either green or blue, and the least safe touch surface being orange or red. Yet another embodiment to distinguish between the safer touch area to the less safe touch area can be where the safer touch area has a green or blue visual signal (and no visual signal for the less safe touch area) or alternatively the less safe touch area being orange or red (and the safer touch area having not visual signal). This latter scenario is less expensive and less energy intensive but fails to provide visual signaling such as preferred to highlight the second person's conscious decisioning making between two choices. Another alternative for the lower safety area is the use of a pigment or paint or even a text graphic specifically indicating an area(s) to avoid touching whether that be of an orange or red color, textured pattern, or the words "do not touch here" (or the equivalent).

Figure 9:
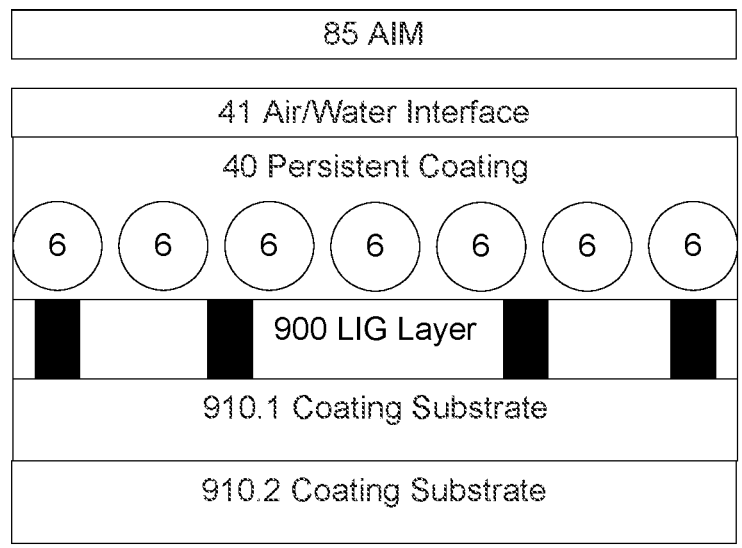
FIG. 9 is a side view depicting a multi-modal DRS including the multi-layer details of the persistent coating.

The operational detail view of FIG. 1 depicts a representative inactivation performance 88 function of at least the parameter of running time since the last touch event of a first person (i.e., user) in the first session. The preferred inactivation performance 88 function has a represented time to reach 1 log reduction of pathogen(s) on the touch surface 10 or persistent coating 40 (of whichever is closest to the air/water interface 41 as shown on FIG. 9), and preferably when achievable a time to reach 2 log reduction as well as time to reach 4 log reduction. The fundamental invention is to maximize the safety of each touch interaction point and has the preferred optional features of AIM 85 enhancement methods, which include the integration of a reactive oxygen species "ROS" generator 75. The ROS generator 75 can in fact be the singular method of AIM 85, but as depicted and in the specifically preferred embodiment the AIM 85 achieves a faster inactivation performance 88 with the addition of ROS for subsequent application onto the persistent coating 40. The ROS generated flowing into a water tank 60, further preferred having water additives 7 (as noted in more detail in the specification) to increase the production of free radicals or the mean lifetime of the free radical, increases the ROS saturation levels of water within the water tank 60. The increase of ROS solubilized within the water accelerates the pathogen inactivation time and since the relative small amount of time between a first persons and second persons touching events is very small compared to the total amount of time in which the operational device is within a user session, the tank 60 therefore decreases the rate of generation of the ROS generator 75 and therefore the size, cost, and peak-power ratings of the ROS generator 75. Gather the water dispersed through either a water sprayer or gravity flow diffuser 50 reduces the maintenance associated with filling a water reservoir (that can double as the water tank 60) by collecting the water in the water collector 55 and further preferred having a water harvester 65 such that the operational device can be self-supporting to further reduce scheduled maintenance activity. The water pump 70 is in water communication between the water collector 55 and water tank 60 (or directly though not shown to the water sprayer or gravity flow diffuser 50. The persistent coating 40 in the preferred embodiment also has embedded additives notably selected from the group of photocatalyst 3, solid acid catalyst 4, increase surface water 5, and/or conductivity (electrical and/or thermal) additives. Yet another optional feature is generation of a differential voltage (whether direct current "DC" or pulsed) between an electrical ground state 92 and voltage in the persistent coating 40 (as shown, though which ever layer is closest to air/water interface 41 as shown in FIG. 9) as powered by the dc power supply 93 (as shown, though can alternatively be an alternating current power supply that is subsequently rectified and pulsed as known in the art). The voltage differential further accelerates the pathogen inactivation time, especially when combined with AIM 85 and ROS generator 75 on the surface further enhanced with water on the touch surface.

FIG. 1 depicts the exemplar where a touch surface is stationary, and a first person interacts with the touch surface followed by a second person touching that same touch surface. Yet, the invention is virtually identical and of equal importance where an individual person introduces cross-contamination with the same potential adverse health consequences by transferring pathogens from a first stationary touch surface to a second stationary touch surface such that the person has an intermediary non-stationary touch surface that transfers pathogens from the first stationary touch surface ultimately to the second stationary touch surface. The DRS in this instance serves the same function of providing a visual signal to the person after touching the first stationary touch surface such that the intermediary non-stationary touch surface has the persistent coating indicating when it is safe to touch the second stationary touch surface. The intermediary non-stationary touch surface can optionally have a AIM 85 as an integral component of the non-stationary touch surface, or alternatively the person can move the intermediary non-stationary touch surface to a stationary AIM 85. In this embodiment the intermediary non-stationary touch surface can be a hand having a persistent coating (such that the persistent coating is similar in nature to a hand-cream operating as a topical mysophobic coating), alternatively the intermediary non-stationary touch surface is a glove, an article of clothing that is outwear, personal protection equipment, etc. The combination of the person "wearing" the intermediary non-stationary touch surface is collectively referred to as another embodiment of an operational device.

Turning to FIG. 2, FIG. 2 depicts an operational highlight view in a top view such that AIM 85 is moved by an actuator 110.1 between a segmented touch surface 10 having at least two segments 1.1 and 1.2 themselves in two distinct positions such that AIM 85 actively reduces the pathogen levels sequentially moving between a first position 120.1 and a second position 120.2 such that the AIM inactivates pathogens on the touch segment 1.1 from the first position 120.1 and the touch segment 1.2 from the second position 120.2. Various types of AIM 85, such as UV-C emitting LEDs can be harmful to the user 130 of the operational device by touching the touch surface 10 and therefore the DRS has a shield 140.1 that isolates the user 130 from the emitted field from the AIM 85. It is optional for the DRS to additionally have a movable shield 140.2 that also moves from a first position to a second position by a second actuator 110.2 to completely isolate the user 130 and any passerby(s) 131 that could also be exposed to any emitted energy from the AIM 85. This movable shield 140.2 provides an absolute safety procedure, even if user ignores any visual signals (not shown in this figure) corresponding to the respective touch segments (1.1 or 1.2) that is critical when the AIM 85 is a high-temperature surface inactivation method that can reach surface temperatures of at least 200 Celsius.

Turning to FIG. 3, FIG. 3 depicts the two distinct exemplary scenarios where the bottom portion having visual signals 2.1, 2.2, and 2.3 are both in optical and physical communication with their respective touch segments (1.1, 1.2, and 1.3) as compared to the top portion having visual signals (2.11, 2.21, and 2.31) projecting onto their respective touch segments (1.1, 1.2, and 1.3). In this figure the relative position of the air/water interface 41 to the persistent coating 40 (being closest to the interface to physically interact with each user(s) actual touch points where transference of pathogens can take place) with each touch interaction being detected by the touch detection sensor 30.

Turning to FIG. 4, FIG. 4 depicts the hardware and operational application programs (i.e., logic engines) integrating all aspects of the DRS. The DRS is depicted in three main component blocks of DRS server 4000 and distributed control system 695, as well as DRS remote computer 4001. It is understood that DRS server 4000 and distributed control system 695 can in fact be in physical (electrical) communications with each other (i.e., at the same location), though not shown in which case the distributed control system 695 requires at the least of a processor 3100, a system memory 3021, and input/output controller 3111, and at least one application program such that the application program at least consists of touch location engine 3210.2, sensor engine 3202, and at least one of persistent coating engine 3200 or AIM engine 3204. The particularly preferred embodiment is where both the DRS server 4000 co-exists with the distributed control system 695 having the required processor, memory, controller as noted above. The DRS server 4000 is optimally in communications with multiple distributed control systems 695 (such that each operational device has its own distributed control system to run real-time minimal processing requirements) and the server 4000 performs more complex and non-real-time applications 3024 in anticipation of switching being a first person (first user) and a second person (second user). The server 4000 has system memory 3021, an operating system 3022, a file system 3023, and program data 3025 (particularly data representing probabilities of users, pathogens of interest, etc.). The server 4000 optionally has a display 3113 to interact with any system users that are co-located with the server 4000. When the server 4000 is not in electrical communications with the distributed control system 695 it also requires a network interface 3112 on the distributed control system 695, though likely of a different communications protocol. When the operational device has an AIM 85 (not shown here) the control system must also have an AIM engine 3204 to coordinate all associated inputs/outputs and parameters associated with the AIM 85. The touch location engine 3210.2 coordinates the real-time and historic records associated with each touch interaction event for each of the touch segments. The sensor engine 3202 coordinates the real-time monitoring of inputs in determining in real-time each physical touch event to determine each of the interaction events and in which touch segment it occurs. The pathogen engine 3201 calculates the pathogen inactivation performance for each pathogen (of interest) based on the running time interval of each touch segment to ultimately determine the AIM 85 operations as well as visual signal for each respective touch segment. The perturbation engine 3203 utilizes information including motion sensor, etc. to determine when the operational device switches between a first person and a second person. The persistent coating engine 3200 determines and calculates the inactivation performance of the persistent coating based on environmental inputs, frequency of touch interaction events, past persistent coating refresh cycles, etc. Finally, the GUI engine 3205 monitors all touch interaction events, timing of such events, probability of next user type, etc. to reconfigure the graphical user interface display (more detail is in FIG. 12). The DRS remote computer 4001, which also can non-optimally be co-located in functionality with the distributed control system 695 or DRS server 4000. The DRS remote computer 4001 has many of the same components as the DRS server 4000 plus an optional augmented reality or virtual reality display 3113.1 that is particularly useful for maintenance or refresh cycles of the operational device where the authentication engine 3210.1 ensures the refresh cycles occur and occur by authorized and certified personnel. The geographic pathogen engine 3211 calculates, coordinates and communicates to the distributed control system 695 pathogens of particular interest, which can be geographical location dependent in addition to seasonal in nature. The user profile engine 3211 calculates, coordinates and communicates the probability of the next user (i.e., second person) that is particularly beneficial when the DRS operational device is a touch screen for a GUI application driven program (e.g., airline kiosk).

A specific embodiment of the DRS is its use in a sink, notably where the touch is on the sink handles (hot and cold, or just one of warm understanding that this temperature can be any single temperature setting). The sink handle as noted in the preceding embodiments is preferably segmented into multiple touch segments. In addition, the sink embodiment includes motion activated control of water flow (i.e., no touch takes place on the sink handles) and yet cross-contamination takes place in the sink itself whether it be water spray or regular water flow on the water-containing side of the sink being exposed to cross-contaminants from the first person hand-washing (or any other washing of contaminated objects such as dishes, surgical tools, etc.) to the next second person. An additional feature of the DRS unique to sinks is a water-flow indicator sensor (i.e., microphone for sound of water-flow, or temperature on incoming water pipe through faucet or temperature on outgoing drainpipe) to determine the last interaction (physical touch by first person, or first person water contamination of water-containing side of sink). The proper determination of the last interaction time leads to the same logic based on running time interval, etc. plus an additional control of intermittent water-flow in sink to increase removal of contaminants within sink by at least 5% (and preferably by at least 25%, and specifically preferred by at least 80%) every water-flow interval time. The particularly preferred water-flow interval time flows water within the sink through an automated water-flow control valve, and specifically preferred such that the water flowing in the sink is infused with ROS as the active pathogen inactivation method. Another DRS controlled mechanism for active pathogen inactivation is UV dosing downward radiated into the sink as well as within the drainpipe. The DRS utilizes the motion sensor to turn off any UV dosing when the UV potentially radiates outward of the sink and presents a potential visual harm to the second person. The DRS controls the active pathogen inactivation method at an interval that is preferably a function of the water turbidity within the drainpipe, where the subsequent water flow is a function of the water turbidity as a function of time including the amount of water turbidity during the first person user session and preferably also a function of remaining water turbidity following the first user session and prior to the second person user session. The preferred embodiment is the water turbidity sensor is the same sensor detecting positive affirmation of the proper working of the UV inactivation method.

Another embodiment of the invention is to provide visual indication of the safest second touch spot on an operational device having at least one of a persistent anti-pathogen coating. It is known within the art that a persistent anti-pathogen coating has a known pathogen inactivation time to achieve a 0.2 log, 1.0 log, 2.0 log, and in many instances (all as a function of pathogen itself) a 4.0 log reduction. Each instance of a persistent anti-pathogen coating also has a different inactivation time when combined with at least one active inaction method (that is a combination a function of pathogen type as well as function active inactivation method). The determination of past touch spots ranges from known in the art methods including touch sensors having at least segmentation of the candidate touch spots, cameras, or even pressure-activated indication where the indication is a function of time subsequent to the prior touch. The DRS is further combined with a database index of touch events tracking the time of touch and the area in which the touch occurred. The visual indication of safest second touch spot(s) varies as a function of time such that the visual indicator provides the safest color indicator based on actual time interval since a prior touch time, with that time interval being a further function of pathogen(s) of specific importance. The optimal visual indicator provides a continuum of levels of safety as a function of color (i.e., green indicates the safest regions, and red indicates the relative to the safest regions the least safe regions). The visual indicator can project onto the operational device, such as by collimated lens for LED lighting, or a preferred visual indicator as an integral component within the operational device such that the touch surface of the operational device is at least translucent or largely transparent (having visible light transmission greater than 70%, preferably greater than 90%).

Whether by reconfiguration of touch spots or visual indicators the inclusion of an active pathogen inactivation method accelerates the time to reach a substantial log reduction of pathogen presence on the touch surface and therefore effectively reduces the time to reduce probability of cross-contamination and therefore it maximizes the frequency of touch time interval between all touches by the first person and the subsequent touches by the second person where the time interval will exceed the log 0.2, or preferably exceed the log 1.0, or more preferred exceed the log 2.0, or even log 4.0 times based on the combination of a persistence coating and an active inactivation method. As known in the art, many active inactivation methods perform better when the resulting ROS or free radicals are largely contained within the touch surface area. Additional active inactivation methods in fact present the potential to harm people and therefore must be shielded from people during the operating time of those active pathogen inactivation method whether those methods be ultraviolet light, microwave, or ozone generators. The optimal DRS which integrates such an active pathogen inactivation method "AIM" enables the touch surface area from a first person's user session to not only be decontaminated but also to shield any passerby persons from harm. Therefore, the DRS reconfigures the position of the first person's actual touch surfaces to a position that enables the AIM to be effective on that first person's actual touch surfaces while the backside of that actual touch surface shields the passerby persons from harm by the AIM and concurrently presents a second touch surface area to the second person for their second person user session. In this manner, the DRS contains or shields the first touch spot prior to pathogen inactivation to not contaminate a second person touching that same first touch spot. An additional benefit of this shielding or containment is to increase the effectiveness of the AIM in the decontamination process on that first touch spot. A particularly preferred embodiment is that the containment or shield of the first touch spot increases the concentration of non-thermal plasma over the first touch spot by reducing the distance between the containment or shield and the surface of the first touch spot such that the backside of a second touch surface area is a component within the AIM acting on the touch side of the first touch surface area. This "nesting" of surfaces reduces the distance between the containment or shield and the surface of the first touch spot while protecting the second person during a non-thermal plasma or microwave energy generation to inactivate any pathogens on the first touch spot. A particularly preferred first touch surface also includes the addition of a catalyst to increase the production of ROS.

The DRS, with its visual indicator(s), provides a novel opportunity to address the fears and lack of power associated with physical interactions of germophobes (i.e., mysophobia) whether the germophobe (knowingly or unknowingly) is the first person or second person (or of course yet subsequent beyond the second person) to engage with the operational device. The DRS uniquely engages with the germophobe (interchangeably being either the first person or second person) by presenting at least two visual indicators where the first of the at least two visual indicators presents a first touch area having an increased safety (i.e., a lower cross-contamination potential) to a second touch area recognizing that the potential for cross-contamination of the first touch area is at least 5% lower than the second touch area (and preferably at least 50%, and particularly preferred at least 80%). It is understood that the DRS recognizes that a germophobe has very little inherent confidence that a third party (or even an operational device with an AIM) provides adequate decontamination of the touch surface area. It is further understood that presenting the germophobe with two touch surface areas with a visual indicator of relative safety between the two touch surface areas gives the germophobe the decision power (and importantly the information) to make an active decision to touch the safer area. Another method of engagement for the germophobe is direct or indirect communication to the DRS controller to obtain critical parameters such as the last time in which the persistent coating was applied, the last time in which the persistent coating was refreshed with new pathogen killing actives, the last time in which the touch surface was disinfected or in which the touch surface had the AIM treatment process applied. The communication between the DRS controller to the germophobe can be directly from the operational device to the germophobes communication device (e.g., smartphone) or indirectly from the DRS cloud communication to the germophobe's such that the germophobe's device provides the precise location via traditional wireless determination or via the camera/sensor authentication of the operational device. The bottom line is the invention provides an increased sense of confidence by explicitly presenting an actionable decision to the germophobe such that the germophobe gains a sense of control by actively utilizing accurate information, for an empowered decision, of the safety of a touch spot relative to the safety of another touch spot.

The DRS also engages with the germophobe through communication means directly (as in DRS to germophobe smartphone device such as Near Field Communication "NFC" or Bluetooth) or indirectly DRS to WiFi or cellular communications to the cloud as known in the art and germophobe using a device such as smartphone taking a picture of a visual identifier or just using its global positioning system "GPS" such that the germophobe (or any person interacting with or passing by) is able to get specific information on the operational device status including most recent time of a first person touch preferably by touch surface area segment, 1 log (or 2 log, or 4 log) time interval with the calculated (or visual indicator associated with) time since an active touch relative to the time interval required for pathogen inactivation. The preferred optional information presents the last time in which a persistent coating has been applied, the last time which a refresh coating to reinfuse the persistent coating with its active, and in a particularly preferred scenario the germophobe uses a smartphone embedded sensor to detect the presence of a pathogen (or the general ATP sensors) or a camera capable of taking a picture such as quantitative PCR and uploading this information to the cloud for calibration of surface inactivation 1 log (and 2 log as well as 4 log) rate curves as a function of time and verification of persistent coating efficacy or a vapor presence sensor particularly for the detection of vapors emitted when the active within the persistent coating is available (and more preferred indicating the potency of the vapor). It is understood that the operational device in its preferred embodiment has an embedded vapor presence sensor capable of detecting the active within the persistent coating to validate its efficacy as a function of time and coating active concentration/availability. The germophobe or passerby serves the role of efficacy validation as a "public" service while concurrently feeling more empowered and therefore more confident in having a lower general sense of contributing to the solution rather than just a passive subject of exposure with the operational device. Active visual signaling both enables the passerby to touch a portion of the operational device that is relatively safest, but also active signaling to the passerby real confirmation the DRS is properly working and visual signals/indicators are legitimate.

When the DRS has direct or indirect communication with the operational device, the system gains the ability to have visual indicators (e.g., LED, or text, symbol etc., within the GUI when the operational device has an active display) that are in fact personalized. The individual passerby may be uniquely susceptible (or concerned) to a specific pathogen, whether it be by fear or due to an existing medical disease state, and therefore the visual indicator with respect to time interval is comparative to the 1 log (2 log, or 4 log) specific to that specific pathogen. The visual feedback to any subsequent person prior to a touch event is now more accurate in its reflecting the safety from cross-contamination as a function of time interval since the most recent touch event, and preferably a visual heat-map showing relative safety within the various physical space in which a subsequent touch event can take place.

A particularly preferred embodiment is such that the DRS has an active method to reduce adhesion i.e., active pathogen repelling method "ARM") between a touch surface on the operational device through the same controller and therefore the potential for transfer of any pathogens from the operational device to the part of the body of the second person to that touch surface. An exemplary active method is the controller capable of varying the touch surface from a positive voltage to a negative voltage, and preferentially to a ground state such that the surface charge increases the creation of ROS, electrostatically repels the pathogen and most importantly reduces the pathogens creation of biofilm or biofouling. The return of the touch surface to a ground state immediately prior to a subsequent physical touch by a first person or second person or germophobe or passerby minimizes the occurrence of an uncomfortable electrostatic charge. Therefore, the best embodiment is a coating have at least 30% of its surface area being a conductive coating, particularly preferred having at least 50%, and the specifically preferred surface coverage has a physical spacing interval of less than 70% of the median length of the smallest pathogen of concern.

Another embodiment with even better performance is such that the DRS has an ROS generating active method that further includes a method or coating composition for the operational device to increase the presence of surface water on the touch surface of the operational device. The availability of water whether it be adsorbed into the touch surface of the operational device or applied (through methods known in the art including spray atomizer, gravity flow) such that the DRS ROS generating active method increases the production rate of ROS/free radicals. The particularly preferred scenario is such that the water is now present near any adhered pathogens so as to have an at least 5% higher (preferably at least 20% higher, and particularly preferred at least 80%) free radical dosing as compared to the active method without the additional water near or on the pathogen. Therefore, the combination uniquely increases the effectiveness of an active pathogen inactivation method.

A further preferred embodiment of the invention accelerates the rate of pathogen inactivation by combining the persistent coating on the touch surface (where the coating is upwards towards the air/water-interface) and an active pathogen inactivation method that acts in the direction towards that air/water-interface in which the coating is applied on the operational device. The combination of a persistent coating that further comprises at least one catalyst (e.g., a photocatalyst notably and preferably a catalyst that is effective in the visible light range) that is activated by the active pathogen inactivation method such that the combined effectiveness (i.e., the time to reach a 1 log, or 2 log, or 4 log) reduction in viable pathogens is accelerated by at least 10% of the time in which each of the individual methods would reach that same 1 log, or 2 log, or 4 log) reduction. The preferred acceleration time is at least 25% faster than the individual method, and particularly preferred acceleration time is at least 80% faster than the individual method.

The specifically preferred embodiment comprises the following: 1) a persistent coating having a 1 log reduction time faster than 2 minutes (particularly preferred faster than 30 seconds) on the air/water interface side of the operational device's touch surface, 2) the persistent coating has an embedded photocatalyst such that light (typically ultraviolet-C "UV-C", or preferably visible light as known in the art) accelerates the 1 log reduction time by at least 10% as compared to without the photocatalyst, 3) the persistent coating is at least hydrophobic (preferably superhydrophobic or at least having superior hysteresis enabling water roll off at least 25% better than without the water repelling properties, and more preferred to have low solid adhesion particularly low adhesion strength of the pathogens of concern), 4) water is applied onto the persistent coating (on a temporary basis such as during the combined pathogen inactivation methods of persistent coating with active pathogen inactivation method operable with the photocatalyst embedded into the persistent coating (and where the preferred water has previously been enhanced with solubilized ROS such as ozone, where the ozone infusion process has the ozone bubbles reduced to a size of less than 200 microns and preferably less than 200 nanometers and particularly preferred less than 60 nanometers so as to maximize the ozone solubility), 5) an active pathogen inactivation method with the emitting field directed to the air/water interface, 6) a water collector/capture method (which would presumably also collect any accompanying inactivated pathogens as well as residual dust, dirt, organics, etc.) so as to minimize subsequent wet touching by the second person as well as minimize water consumption in addition to substantially increasing the time in which pathogens can become inactivated as any remaining ROS will continue to inactivate the pathogens within the water collection holding tank. The holding tank "tank" has a fundamental advantage of increasing the amount of ROS in the water during periods of time in which the first person or second person(s) are utilizing the operational device such that the pathogen inactivation time between the operational device use by the first person and the subsequent second person is substantially reduced. It is understood that the DRS calculates the running interim time and projects the arrival time of a second person so as to determine when the active pathogen inactivation method is required to operate and that the persistent coating is not sufficient to inactivate the pathogen prior to the later of the arrival time of the second person or more specifically the projected touching within the touch segment of the operational device touch surface. The operations of the active pathogen inactivation method consumes resources, at least being electricity and in the optimal embodiment also water, therefore particularly where the operational device obtains its energy source from relatively limited sources such as wireless power, photovoltaic solar cells, or onboard batteries, it is a function of the DRS to utilize the projected time interval between a first person's touch last touch and the second person's first touch (within the same touch segment) to reduce the operating frequency and time duration of the active pathogen inactivation method. The DRS uses the following: 1) historic user session time including the historic user session segmented with the individual touch segments within the touch surface of the operational device (and more optimally the historic records are segmented by type of person e.g., domestic airline traveler vs. international airline traveler), 2) probability index of type of person as a function of time of day, day of week, holiday calendar, etc. such that the combination of #1 and #2 yield a superior projection of projected time interval, 3) non-contact registration queue by the second person prior to physically interacting with the operational device (which can occur by method known in the art including GPS, wireless communications triangulation, or even ping communications between the second person's smartphone and the operational device using short-range wireless communications including low-energy Bluetooth, NFC, or the effective equivalent) such that the precise second person type is known which enables the operational device and the DRS to know precisely the nature of the physical interaction will be rather than having to use historic records to project (i.e., knowing that the second person is a domestic passenger vs. an international passenger will both provide the DRS a more accurate prediction of session time, knowing which subset of touch segments are more likely to be utilized in the upcoming user session, and therefore more precise knowledge of which touch segments are required for better placement or selective placement of the active pathogen inactivation method over those touch segments in which insufficient projected time intervals can't be achieved with the persistent coating alone).

The photocatalyst as an integral component to the persistent coating has a benefit when the photocatalyst is itself hydrophilic as the photocatalyst actually on the coating surface at the air/water interface such that water (preferably with solubilized ROS) would remain (even as small droplets of less than 500 microns, particularly less than 50 microns) has the benefit of increasing the rate of free radical creation for the combination of the active pathogen inactivation method such that the hydrophilic nature of the photocatalyst will maintain intimate contact with water flowing or sprayed on the operational device touch surface (or specifically in previously touched touch segments of the overall operational device touch surface) to increase the ROS generation at sites that have the highest potential adhesion of pathogens. Another embodiment, though opposite is where the photocatalyst (or other ROS generation catalyst) is modified to be hydrophobic and therefore flowing (or sprayed) water rolls off the surface minimizing the residual water remaining on the surface. The rolling off water will flow over any solid remaining on the touch surface, which notably includes pathogens that are to be inactivated by the active pathogen inactivation method. Some residual water, preferably with the solubilized ROS will remain on the pathogens and therefore selectively wetting the pathogen surface leading to accelerated inactivation time (as compared to without the active pathogen inactivation method.

It is understood that most references to a photocatalyst can be exchanged with a solid acid catalyst, that eliminates any residual water being acidic on either the first person or second person's hand after interacting with the touch surface of the operational device. A preferred embodiment has salts to create dissolved ions/solids in the water flowing over the touch surface to further accelerate the pathogen inactivation time, where the salt content is at least 0.01% on mass basis and preferably at least 1.0% on a mass basis of the total water mass. The particularly preferred photocatalyst or solid acid catalyst is functionalized with a fluorinated compound (specifically preferred to be a fluorinated sulfonic acid) such that the catalyst migrates to the air/water interface. The specifically preferred photocatalyst is activated by light in the visible spectrum. And the extra specifically preferred photocatalyst is embedded in the coating, is wet with an ozone saturated water, and is activated by visible light, and creates oxide products that oxidize any organic material on the operational device touch surface notably pathogens. The water can further other additives including acetic acid (i.e., vinegar) as being a food grade solvent. The presence of oxygen in the water further enhances the oxide co-products. The further presence of metal powders in water, notably food grade micronutrients for enhanced safety include cobalt, manganese, molybdenum, and zinc as nanoscale powders.

It is understood that water can be obtained via known in the art atmospheric water (water harvester) techniques so as to obtain water without requiring ongoing filling of a water reservoir, particularly given that the quantity of water consumed is very low. Atmospheric water methods include the use of metal-oxide frameworks "MOFs", zeolites, as well as enhanced condensation coatings on a Peltier thermoelectric cooler device. The zeolites have a particular advantage in that resistive heating releases water that is simply obtained by adsorption from the atmosphere and is a solid acid catalyst.

The combination of at least the running time interval for each touch segment and a persistent coating on that individual touch segment and the DRS providing at least visual feedback to a second person reduces the cross-contamination of sequential touches by at least 5%, preferably at least 25%, and preferably at 50%, and particularly preferred at least 66% such that the visual feedback increases the switching interval time for that respective touch segment by increasing the running time interval.

The DRS in its simplest embodiment provides a dynamic control of a touch surface segmented into at least two segments within an operational device and then presentment of visual indicator indicative of the cleanliness of the respective touch segment with relationship to 1 log (or 2 log or 4 log) pathogen inactivation in accordance to switching interval time and pathogen inactivation method whether it be the persistent coating or the active pathogen inactivation method. The DRS utilizes the time subsequent to a first person's touch to: 1) determine or predict if this is the last touch event for the first person, which is based best achieved by a motion sensor or first person terminating the user session (e.g., a specific task on a graphical user interface such that the controller operating the task at hand knows the specific sequence of events for that task at hand, including an equivalent to first person indicating task at hand completion) or in its absence (interchangeably "void of") where the DRS or task at hand controller uses a probability index to predict how long a user session is typically such that at least planning of any active pathogen inactivation method can be ready (i.e., in queue), 2) project the switching time interval between the last touch event of first person and the first touch event of the second person (which is only necessary when the DRS is also controlling the activities of an active pathogen inactivation method, and 3) active control of visual indicators based on the time since the actual last touch event of the first person in combination with the 1 log (or 2 log or 4 log) reduction of active pathogens based on either just the persistent coating or standalone active pathogen inactivation method, or the combination of the persistent coating 1 log (or 2 log or 4 log) as a function of time for each active pathogen inactivation method (and any intensity parameter(s) or other performance parameters that determine the rate of pathogen inactivation), 4) the DRS continues to regulate the visual indicators at least until such time as a next touch event takes place such that the visual indicator is optimally best for each touch segment within the touch surface of the operational device. It is further understood that the rate of pathogen inactivation is pathogen specific and thus the DRS also varies the regulation of the visual indicators by at least one pathogen selection method of a) worst-case scenario, b) highest-probability within the geofence of the operational device based on historic records, c) pathogen of highest concern to the general population or population within the highest probability of interacting with the operational device or pathogen of highest safety risk or when the identity of the second person is known the pathogen of highest safety risk is for that known second person, and then 5) regulation of the visual indicator that transitions during the time subsequent to physical touch (preferably by actual touch sector/segment) through completion of persistent coatings or decontamination (interchangeably with pathogen inactivation) method or multi-modal pathogen inactivation method in accordance to a) disease (interchangeably with pathogen) of noted interest and time in which decontamination method takes to prevent the disease from replicating at least in-vivo of the second person (and preferably also on the surface in which second person will subsequently touch where the disease probability is specific to that second person/individual projected to touch the touch surface of the operational device. The DRS regulates the visual indicator for both the surface area(s) in which decontamination takes place to the fullest extent possible as well as at least a less effective decontamination area (or indicating passively or dynamically an area in which no decontamination takes place), so as to communicate visually to the second person an effective touch decision option to the second person. The presenting of at least two touch surface areas for the second person to make an active decision of where to touch or at least where not to touch increases the second person's confidence and/or reduces the second person's stress level by the second person making an active touch decision (i.e., this gives the second person a stronger by at least 5% sense of empowerment, preferably at least 25%, and specifically at least 50%) to reduce the stress level by at least 5% (preferably at least 25%, and specifically at least 50%).

One embodiment of the DRS has a transparent window between the second person and the touch surface of the operational device (e.g., decontaminating salt and pepper shakers on a table at a restaurant, etc.) in which one such active pathogen inactivation method is the exposure of UV-C that could be harmful to the second person approaching or the first person leaving the operational device respectively or food products in proximity to the operational device. In this embodiment the substrate layer closest to the consumer (collectively the first person or second person) is UV blocking or reflecting while the receiving (object being exposed to by the UV-C source) layer(s) on an exemplary salt- and pepper-shaker has a substrate layer closest to the food product that is UV diffusing or reflecting (or even UV absorbing) so as to minimize creation of free-radicals within the food product.

Figure 6:
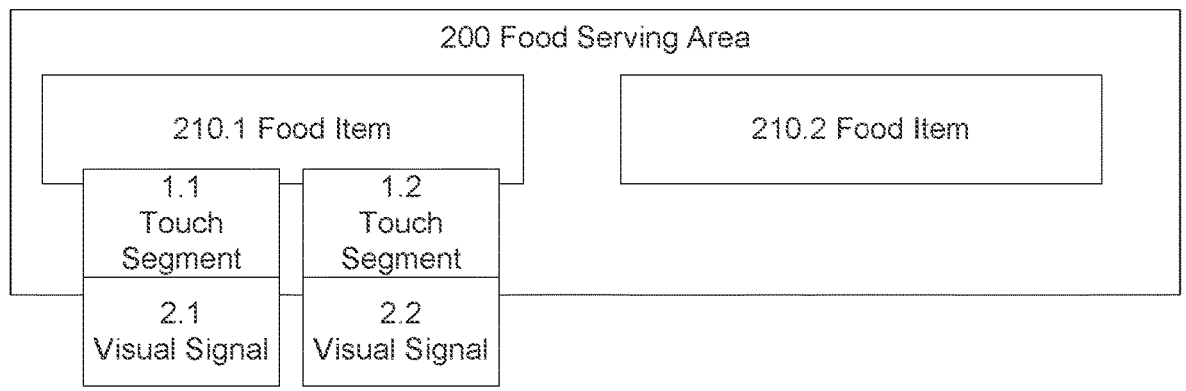
FIG. 6 is a top view of a food serving embodiment of the DRS.

Turning to FIG. 6, FIG. 6 is an exemplary food serving area 200 from the top viewing perspective, such as a salad bar, a cafeteria line, a buffet, or even a food preparation area in a fast casual restaurant, having at least two food items 210.1 and 210.2 where the exemplary food item 210.1 shows two serving utensils (i.e., they move independently of each other so are technically two distinct touch surfaces) still represented as touch segment 1.1 and 1.2 as the DRS still determines which touch segment is safer between the two touch segments within the same food item 210.1 to touch and provides a visual signal 2.1 and 2.2 to each of the touch segments 1.1 and 1.2 respectively.

Figure 7:
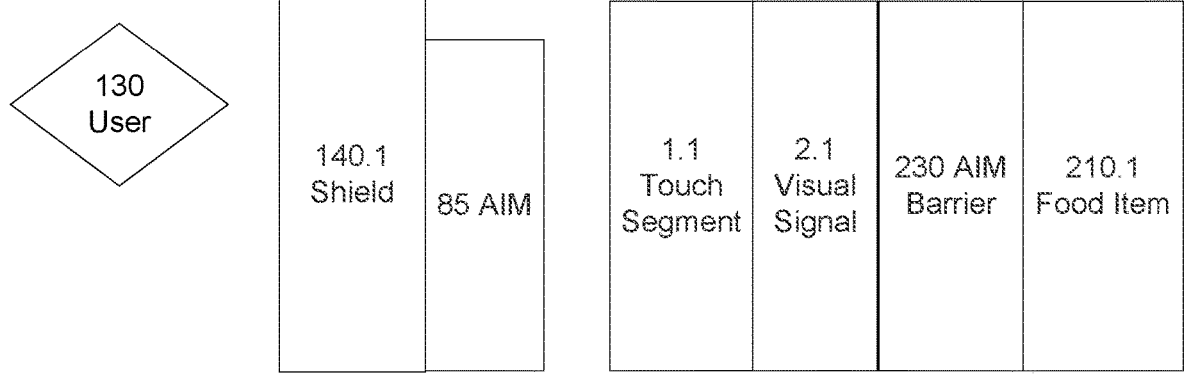
FIG. 7 is a side view of a food item (or generally any component that needs protection) from the AIM emitting zone.

Turning to FIG. 7, FIG. 7 is a side view perspective for a food item 210.1 such that the container/packaging for that food item further includes an AIM barrier 230 layer such that the emitted energy field does not create harm (notably free radicals which accelerates oxidation damage) to the food item 210.1. It is understood that the food item 210.1 can be replaced with any object that is damaged by exposure to the AIM 85 emitted energy source. When the AIM barrier 230 is not transparent or translucent the visual signal 2.1 is outward facing of the food item 210.1 and AIM barrier 230. There are multiple embodiments to detect user 130 touch interactions with the food item (i.e., touching the container/package) with the touch interaction being represented as a physical touch on the touch segment 1.1. It is understood that multiple methods are anticipated to detect touching take place, including a weight sensor in which the food item 210.1 is placed on, a touch sensor within the container/package, a motion sensor detecting the movement of the food item 210.1 from a first position to a second position, etc. The DRS controls the activity of an optional AIM 85 which is on the inward-facing (towards the food item 210.1) relative to the use 130. As noted in other exemplary scenarios, the AIM 85 method often requires shielding to limit exposure to the user 130 by having a protective shield between the AIM 85 component and the user 130.

Figure 8:
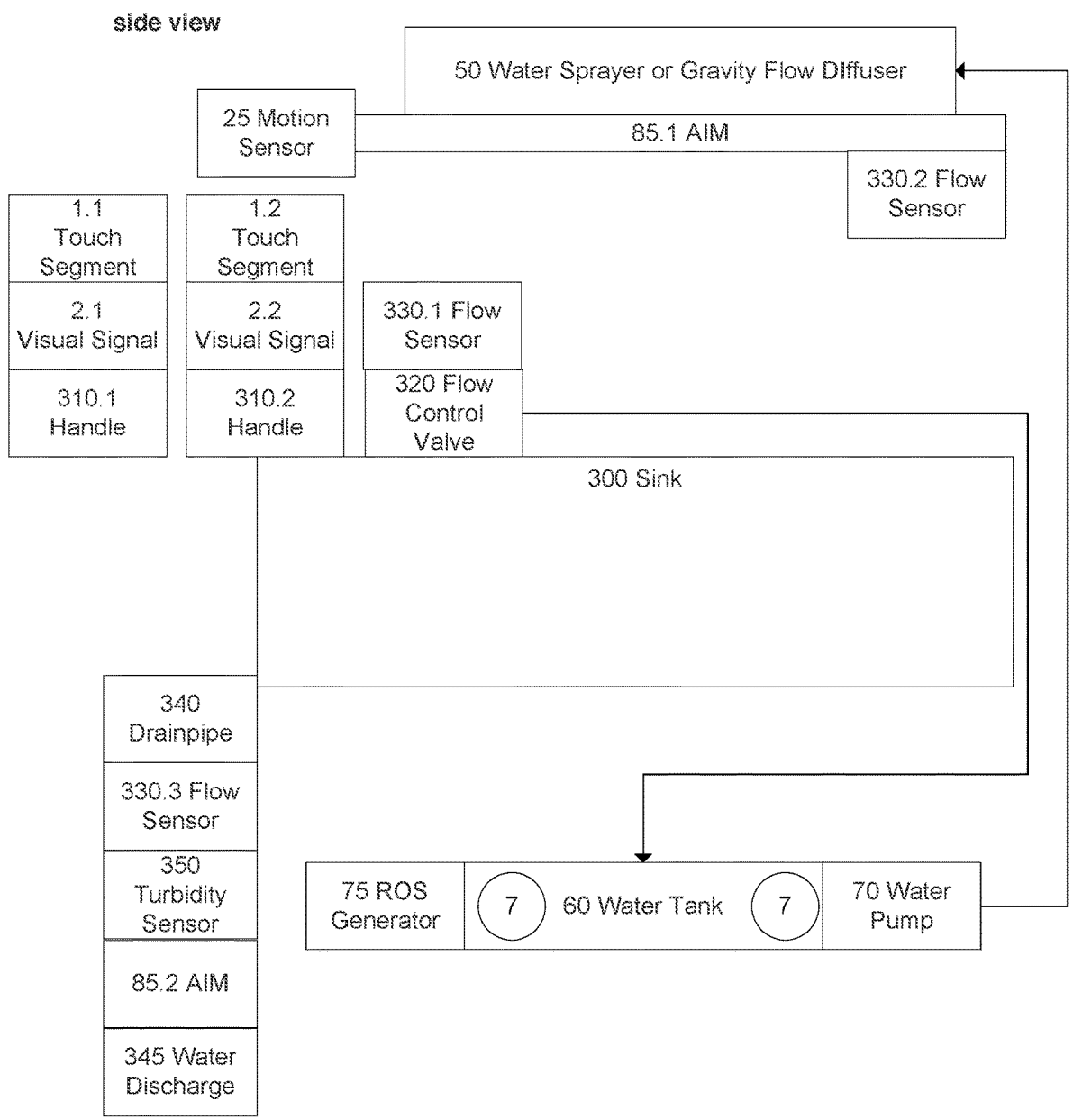
FIG. 8 is a side view of a sink embodiment of the DRS.

Turning to FIG. 8, FIG. 8 depicts the instance of DRS for the operational device being a sink (whether that be sink in the kitchen or in a medical facility. The sink 300 interior (water containing) is in either physical or functional communication with water flow control through the flow control valve 320 of through a multi-touch segmented handle 310.1 and 310.2 (each having optical communication between the respective handles and the visual signals 2.1 and 2.2. The touching of the handle's touch segments 1.1 and/or 1.2 has the same functional capacity as the other embodiments of the DRS, though alternatively the flow control valve 320 activated by a motion sensor 25 (or a foot pedal, though not shown) provides the equivalent operational sequence in terms of regulating water flow analogous to a physical touch interaction by the user. There are multiple methods, all by flow sensors to detect actual water flow, independent of the touch detection method or in fact whether a physical touch actually took place. The flow sensor 330.2 embodiment is an indirect method that can include a microphone or a camera. The flow sensor 330.1 embodiment is integral to the incoming piping that discharges clean water into the sink 300. The flow sensor 330.3 embodiment is integral to the outgoing drainpipe 340 in water communication upstream to the sink 300. The AIM 85 emits its radiated energy field (whether that be ion generator, or UV-C light). Though not shown in this figure, it is understood that the sink 300 can be lined with a persistent coating as noted in the other embodiments to increase the effectiveness of pathogen inactivation. The functionality of the respective water components that are in water communication with the ROS generator 75 is identical as noted in FIG. 1, and therefore not repeated here. The further feature leverages the turbidity sensor 350 such that the DRS intermittently activates the AIM methods 85.1 (as noted earlier, including in FIG. 1) to inactivate pathogens in the sink 300, and/or AIM 85.2 (preferably a UV-C method) such that pathogens residing in the drainpipe, after the stop of water discharge into the sink, are also inactivated. A particularly preferred embodiment has the turbidity sensor 350 also being an AIM 85.2 operational validation prior to the water being discharged into the water discharge 345.

Another embodiment of the DRS controls an actuator and/or GUI display reconfiguration of touch points within the overall touch surface of the operational device such that the actuator or reconfiguration moves the cross-contamination surface from a first position for the first person to a second position for the second person to increase the time interval between subsequent touch points (e.g., kiosks, door handles, pitchers, elevator buttons, etc.) by at least 5% (and preferably by at least 25%, and particularly preferred by at least 80%, and optimally preferred by at least 200% such as could be obtained by just switching touch surfaces amongst 3 available touch surfaces). The GUI display reconfiguration recognizes that sectors/segments within the active touch area are often sequential (i.e., physical touch to enter numbers prior to physical touch of an "enter" button). The relative movement of the "enter" button in which a non-DRS enabled system is present has every user touching the same touch point at the conclusion of their respective user session, therefore the reconfiguration of the "enter" button is the most important portion of the touch screen. Determination of the reconfiguration can also take place by probability of sequential intervals based on a historic record such that a primary task/function of the second area is moved to the first area in which a prior touch took place to maximize the time interval in the first area. The optimal DRS enabled GUI display maximizes the actual touch points to occur within a touch surface area that occupies as small of a place within the overall touch surface of the operational device, therefore enabling the GUI display to be partitioned in as many as practical segments within the overall touch surface area therefore leading to the maximum amount of switching time interval between first person to second person (and as understood between third person and then fourth person and then fifth person, etc. with a general understanding that cascading sequential person(s) are noted as still being first person followed by the second person where in reality it is first person followed by second person followed by third person and so on.

Yet another feature of the DRS is to monitor, control and to coordinate a refresh cycle on the persistent coating. A refresh cycle is a task in which the active contained within the persistent coating, as known in the art, is infused into the persistent coating so as to reset the speed of pathogen inactivation to close proximity of the original speed of pathogen inactivation at the time in which the persistent coating was applied onto the operational device. Since the preferred persistent coating is fast acting, preferably having a 1 log time shorter than 5 minutes (and particularly preferred shorter than 2 minutes) and a 2 log time shorter than 10 minutes (and particularly preferred shorter than 5 minutes and a 4 log time shorter than 15 minutes (and particularly preferred shorter than 12 minutes) it must be refreshed more often. In fact contrary to traditional persistent coatings (such as having a silver or copper or zinc active) that have very long periods of time in which persistency lasts (i.e., many weeks if not months or even years), the preferred persistent coatings for very high frequency touch points (where the switching time between subsequent users can be less than 30 seconds) are much better having 1 log time shorter than 15 seconds and yet needing a refresh cycle on a daily or even hourly basis (though likely once per day should be adequate). Regardless of how often the refresh cycle needs to take place, it is a fundamental feature of the DRS to ensure that the refresh cycle actually takes place prior to the active within the persistent coating is fully depleted (i.e., less than 20% residual remaining within the coating, or less than 5% residual remaining). The rate of active being depleted is a function of at least one parameter from time, temperature, atmospheric pressure, light-level exposure (especially direct solar UV exposure), and cumulative number of touch points within the touch surface/segment as well as pressure applied during the touching of the touch surface/segment, or in the preferred embodiment an embedded vapor presence sensor detects the presence of the active within the persistent coating. The DRS features a process to authenticate the task of refreshing the persistent coating that includes verification of the time of refresh cycle preferably by an authorized cleaning person, with the further feature of using both the same touch sensors/segments for the purpose of calculating switch time interval, running time interval for each segment as used to validate the amount of time in which the refresh cycle took place (as by touch segment) and particularly preferred such that the touch sensor detects the presence of a wet refresh formulation being applied on the touch surface/segment. This process is best done by a certified and trained person for refresh cycle operational task and therefore the DRS also validates the refresh cycle being done by such an authenticated refresh-cycle person. The optimal DRS feature set enables a location identification tag (cross-referenced) with an actual geofence determination (via location accuracy) as a two-factor validation method to verify the refresh took place for at a minimum each operational device. The DRS as noted before has a sensor means (preferably the same as the touch sensor) to validate presence of sufficient refresh cycle active within the refresh solution to be applied on to the operational device. The type of decontamination active (i.e., a passive method, relative to the active pathogen inactivation method) within the persistent coating for pathogen inactivation) as well as mass percentage of the active within the refresh cycle solution in addition to calculated amount of remaining active within the persistent coating at the time of refresh cycle is calculated or projected by the DRS in order to improve the accuracy of the infused amount of active within the persistent coating on the touch surface/segment of the operation device, which is vital to determining the actual 1 log (and 2 log and 4 log) times as this is essential in determining the minimum amount of safe switching time between first person and second person, which is then subsequently vital to determining the control of visual indicators and/or scheduling of active pathogen inactivation method. The preferred embodiment further has a sensor to calculate the active intensity detection on the persistent coating so as to improve the calculated decontamination time required between a subsequent last time in which the first person has a first touch event in the first user session and the first time in which the second person has a second touch event in the second user session.

All of the aforementioned features and procedures improve the accuracy of the visual indicator such that a first active touch surface after being physically touched changes to a cleaning visual indicator and the second active touch surface changes to a select visual indicator (such that the person/user has visual indication of at least relatively decontaminated/pathogen inactivation areas) to minimize the probability of cross-contamination leading to real decreases in pathogen cross-contamination via the operational device. The visual indication is also relevant on a first active touch surface that is moved into a second position or simply stationary providing an authenticated signal to each person that sufficient time has passed to inactivate pathogens since the last touch event.

A preferred multi-position operational device has at least two positions in which a user is only able to interact with one position at a time, and the DRS moves between the at least two positions immediately after the last touch event of a first user and prior to the first touch event of the second user. The operational device also has a shield or containment object such that the shield or containment object limits exposure of an active pathogen inactivation method on the operational device while decontaminating the first position while the second user interacts with the second position. One exemplary inactivation method is UV-C in which the shield (can be visible light transparent, while UV absorbent) blocks the UV line (to block harmful rays) of sight to the current user and preferably also to any passerby persons that are in proximity to the operational device. Another exemplary inactivation method is a voltage applied on the touch surface where the DRS in combination with a motion sensor or proximity sensor/device such that inactivation/decontamination method is temporarily stopped (or electrically grounded) so as to prevent adverse impact on a subsequent user/person in close proximity to the operational device. In this manner an electrical or static shock due to voltage presence, or a high-temperature activated surface (approaching a maximum temperature of 300 Celsius, or even 250 Celsius, or even 150 Celsius such that the higher maximum temperature is needed to decrease the required time to inactivate any pathogens present) on the active touch surface is not experienced by the next/second user. The utilization of PPG Teslin product enhances static discharge as known in the art, as well as graphene embedded polymers or coatings.

Yet another embodiment of an at least two position AIM component within the DRS controlled device is a coating comprised of at least one of conductive additive including graphene, boron nitride nanotubes, carbon nanotubes such that the coating is at least one of electrically conductive or thermally conductive predominantly in the in-plane direction (as opposed to through-plane) preferably having a thermal conductivity in-plane to thermal conductivity through-plane ratio of at least 2:1 (and particularly preferred at least 4:1 and specifically preferred at least 10:1). The preferred conductive additive is a planar conductive additive that maximizes in-plane conductivity and (aligned with the persistent coating film forming direction) is in the bulk portion of the persistent coating (i.e., bulk meaning as an additive throughout the persistent coating). The preferred embodiment of this AIM device has the conductive coating, the layer closest to the air/water interface i.e., "top-coat", with a coating/substrate layer immediately below it consisting of at least one of a: a) phase-change material to reduce the heating of the bulk of the operational device and to reduce the temperature gain of the bulk of even the coated surface, b) thermal barrier coating to limit heat transfer from the top-coat into the operational device to maximize the cooling of the top-coating to prevent injury to the user and/or return to normal operating mode of the operational device (i.e., ready for second user), c) "cooling" plate having a liquid circulating to rapidly dissipate thermal energy from the top-coat, d) low thermal conductivity ceramic, high-temperature rated polymer (e.g., aramid), and/or e) high-emissivity having a normal thermal emittance of greater than 0.80 (and particularly preferred greater than 0.90 and specifically preferred greater than 0.95). The particularly preferred substrate has a thermal conductivity less than 20 W/mK and a normal thermal emittance greater than 0.90 and a melting temperature greater than 300 Celsius and a thermal conductivity through-plane to thermal conductivity in-plane ratio of greater than 3:1. This coating is hereinafter referred to as a thermally isolated high emissivity multi-layer film "TIHEM" film. The TIHEM film can be applied onto virtually any operational device in which cross-contamination can exist, which includes clothing, personal protection equipment (e.g., protective masks, gloves), patient lifts, blood-pressure equipment including the cuff, patient thermometers, serving utensils, gym equipment in public gyms, bed linens, wallpaper, curtains and additionally all of the aforementioned operational devices (e.g., doorknobs, elevator buttons, bed rails, tabletops, countertops, toilet seats, seating and its armrest, etc.). It is understood that each of the operational devices is best powered through wireless power and is controlled by the DRS so as to ensure safe operation (i.e., to prevent burning). The fundamental TIHEM film has a very low specific heat capacity (J/kgC) preferably less than 1000 (and particularly less than 900, and specifically preferred less than 500). All things equal a lower through-plane thermal conductivity is also desired, though a higher in-plane thermal conductivity will reduce hot-spots via thermal spreading. It is understood that the TIHEM film is powered preferably by an integrated wireless power receiver, or alternatively an energy source in electrical communication with a power cord or electrical energy storage device (e.g., battery).

One such method of creating the ideal top layer is a coating precursor comprised of lignin, applied as in a solvent system such as tetrahydrofuran "THF" or other known in the art solvents for lignin. A laser, also as known in the art as laser induced graphene "LIG", is used to create a continuous conductivity array (yielding higher effective conductivity) in an array pattern that becomes a non-planar continuous conductivity circuit (i.e., continuous electrical or thermal circuit) such that the minimum spacing of the matrix has individual, homogeneously arranged arrays smaller than the diameter of a virus (~60 nm) or at least smaller than the diameter of a bacteria (~300 nm). A more practical method is to integrate a high mass fraction (at least 40% by mass) of graphene within the bulk lignin (or lignin and polymeric binder) so that electrically conductivity is ensured by the laser induced graphene but the bulk graphene is able to heat up to at least 250 Celsius throughout the entire surface so as to inactivate the pathogens on the surface without the excessive cost of obtaining a very high surface area treatment of the operational device air/water interface layer by the high capital laser processing equipment. An alternative to the homogeneously arranged arrays being smaller than the diameter of a virus is that the TIHEM topcoat is comprised of bulk thermal conductive additives (e.g., graphene etc.) facing the air/water interface and the bottom side of the topcoat has laser induced graphene at a larger spacing within the homogeneously arranged arrays than otherwise needed to inactivate viruses (i.e., greater than 60 nm, preferably greater than 1 micron, and particularly preferred greater than 50 microns) so as to minimize the resistive heating within the LIG so as to maximize the homogeneity of the surface temperature without the much greater time associated with the operating time of the laser (and thus the much higher cost per surface area). Having the LIG on the bottom of the topcoat prevents surface damage to the graphene due to abrasion. Though the LIG can also be on the top of the topcoat with a deeper penetration (at least 1 micron, preferably at least 5 microns) such that a portion of the graphene remains due to protection by the non-laser treated portion having a slightly higher thickness remaining post laser processing as compared to the portion processed by the laser. This same laser processed portion effectively becomes perpendicular to the air/water interface. The preferred LIG is done on a polymer already having graphene present where the laser induced graphene increases the continuity between graphene in polymer and source of heat spreading or electrical continuity.

Turning to FIG. 9, FIG. 9 is a side view that further details the persistent coating 40, including again noting the persistent coating being closest to the air/water interface 41. This embodiment of the persistent coating has conductivity enhancements 6 (particularly thermal, though with sufficient electrical conductivity to realize resistive heating) in the bulk portion of the polymeric persistent coating 40. The persistent coating 40 primary functionality in this instance is to very rapidly heat any materials, notably pathogens, remaining on the surface of the persistent coating through in-plane heat spreading and to "leak" preferably towards the air/water interface 41 as opposed to through the LIG layer 900 and further down towards the at least one coating substrate 910.1 and the optional though optimal 910.2. The fastest heating is achieved by the further LIG layer 900 such that the enhanced conductivity continuity, relative to the conductivity within the persistent coating 40, also for more homogeneous distribution to reduce or eliminate hot spots. The preferred 910.1 coating substrate is a high-emissivity coating such that thermal energy is radiated towards the air/water interface 41 instead into the operational device thermal mass itself. The optional though preferred second coating substrate 910.2 (which is furthest away from the air/water interface 41) integrates phase change additives so as to reduce the temperature gain realized when the AIM 85 is cycling on. The LIG layer 900 is a coating where a matrix (having conductivity continuity) is made by selective laser processing so as to reduce the cost. The black segment within the LIG layer 900 represents lines of graphene within the bulk polymeric matrix, which also has the advantage of leveraging the low thermal conductivity of polymers again to limit heat transport into the operational device itself. This embodiment of graphene placement, away from the touch surface, also serves to protect graphene from abrasion and therefore enhanced durability.

Figure 10:
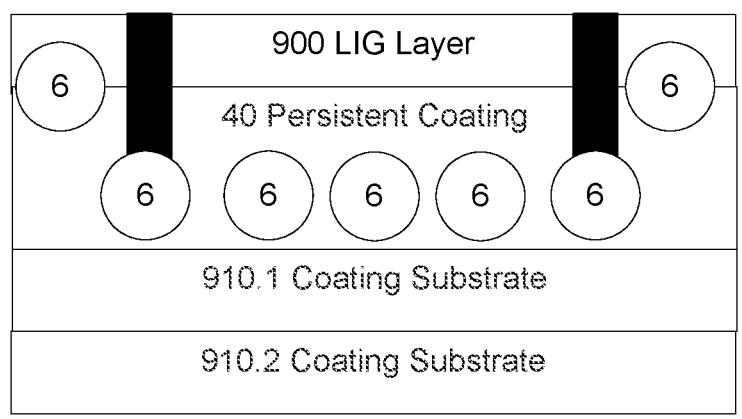
FIG. 10 is a side view depicting another embodiment of the multi-layer details of the persistent coating specific having higher thermal or electrical conductivity.

Turning to FIG. 10, FIG. 10 is largely identical to FIG. 9 and thus the details that are different are limited to the LIG layer 900 being closer to the air/water interface 41. In this instance the LIG layer is comprised of a polymer matrix having high thermal conductivity additives preferably being separately produced graphene that in turn during laser processing will create conductivity continuity across the entire touch surface. The ideal embodiment is such that the spacing of the LIG is approximately of the length scale of the smallest pathogen desired to be killed, which for viruses is on the order of ~60 nanometers. However, that remains expensive to process, and thus a spacing as large as 10 microns is anticipated to still achieve the benefits associated with the embedded graphene. Not having full surface coverage has the further advantage of non-laser processed surface area provides abrasion barrier by the polymer itself thus limiting the depth of abrading away the graphene from the surface and therefore having the highest emitted thermal energy towards the air/water interface 41.

The further preferred embodiment is further comprised of an additional quantity of conductive additive relatively perpendicular to the air/water interface to maximize both thermal dissipation into pathogens on the surface while also maximizing thermally emissivity to accelerate touch surface cooling such that the touch segment is ready to be touched safely by a second person at least 20% faster than a coating void of the conductive additive relatively perpendicular to the air/water interface, preferably such that the ratio of conductive additive in the bulk of the coating to the additional quantity of conductive additive relatively perpendicular is at least 2:1 and particularly preferred at least 5:1. The DRS calculates the real-time surface temperature monitoring through the inherent thermal conductivity which increases as the actual surface temperature increases.

Figure 5:
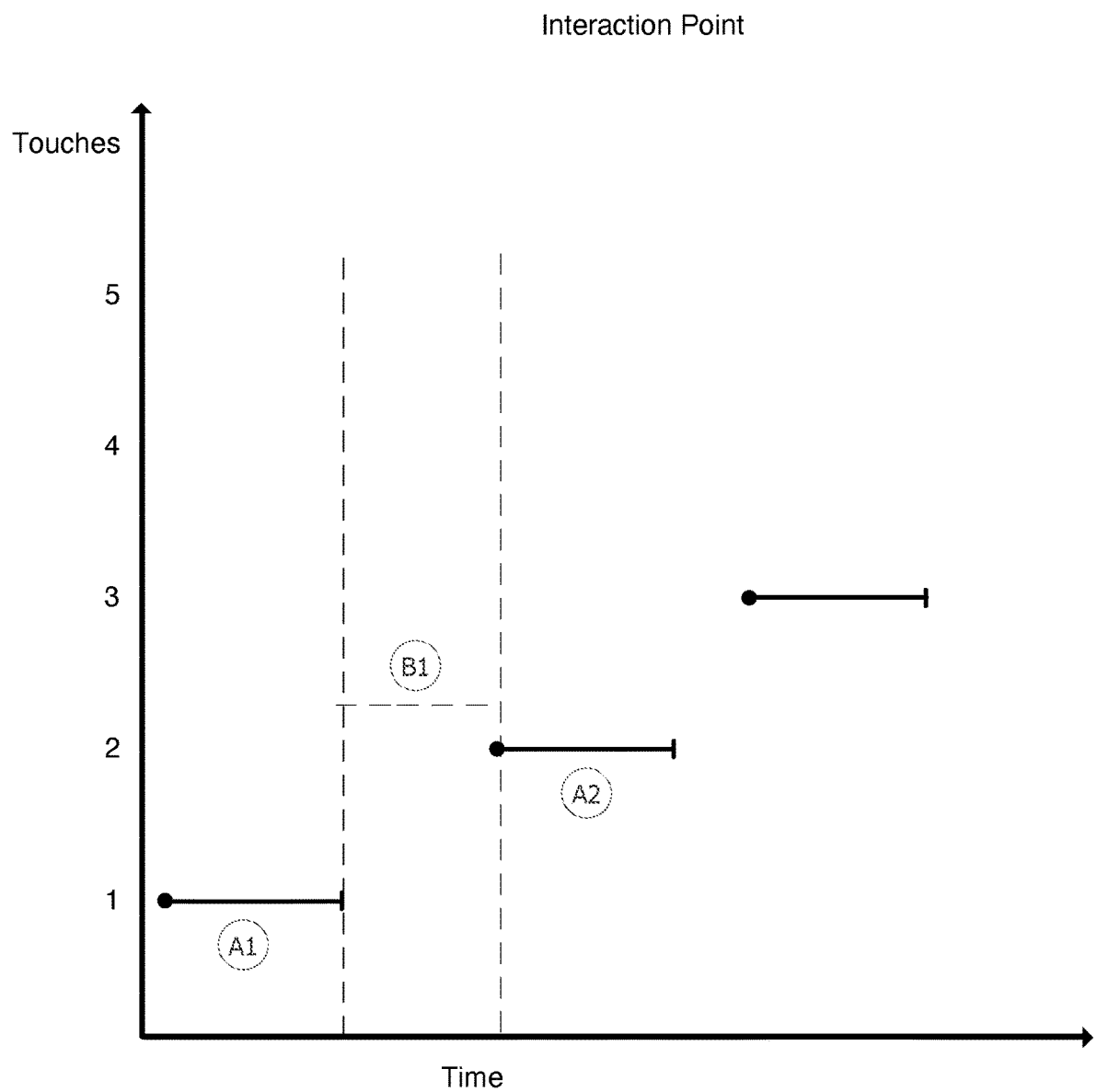
FIG. 5 depicts the time sequence parameters associated with sequential touch interaction points.

Turning to FIG. 5, FIG. 5 depicts a time log, such as in a database, for individual sequential touches for a specific interaction point. The X, Y chart, which has time on the X axis, depicts the starting time of each touch, the ending time of each touch (therefore a calculated duration of the touch (A). Each subsequent touch also establishes the duration between each touch (B). It is understood that a series of parameters are calculated including the average duration of each touch at the specific interaction point, the mean duration of each touch at the specific interaction point. The combination of this database of touches per interaction point with a database of disinfectant treatment (preferably PD treatment) establishes, as per each disease state, the probability of cross-contamination between each subsequent touch that occurs at an interval less than the time required for minimum decontamination (or time required for complete decontamination). Though not shown, it is understood that the host of each touch is a parameter within the database such that the host has a PSI(t) and NSI(t) at that time. The probability of cross-contamination is further a function of each host's PSI(t) as well.

Turning to FIG. 10, FIG. 10 depicts an X, Y plot for the interaction point (per each disease state, at least as differentiated by time and performance characteristics) for the applied decontamination treatment protocol. The plot shows each instance of an applied decontamination treatment (with or without indicative individual touches $A._1$. $A._n$ as shown) in which the duration of effectiveness (A) is the time difference between the start time of effectiveness and the end time of effectiveness (understanding that the rate of effectiveness may diminish as per FIG. 7 over time). The duration between decontamination treatments (B) is critical, particularly in the event that the subsequent decontamination treatment is applied (such as indicated by (D), where touches $A._6$ and $A._7$ are shown) after the prior decontamination treatment has lost effectiveness. This clearly would be indicative of an act of neglect within the environmental aspect of the healthcare facility. These touches\ therefore become perturbations that are a disturbance amplification (i.e., it increases the probability of exposure to the host of touch $A._7$ from the transmitter host of touch $A._6$). A perturbation such as touches $A._3$ and $A._4$, as indicated by (C) is a disturbance rejection (assuming that these subsequent touches are spaced out sufficiently that the applicable disease from host $A._3$ had sufficient time to be completely decontaminated prior to the incidence of touch from host $A._4$) meaning the probability of cross-contamination approaches zero.

Another embodiment with the UV-C active pathogen inactivation method is the touch surface(s), particularly the persistent coating base polymer being comprised of Cytop® from AGC Chemical Company as a particularly preferred UV transparent polymer. The optimal Cytop® composition further includes a binder of UV absorber additive to increase the generation of free-radicals (i.e., ROS) such that the active pathogen inactivation method using a UV-C source strikes the pathogen to be inactivated directly and then as a second active surface in which the pathogen/microorganism of target disease state has a first inactivation pass (UV-C direct line of sight) and second inactivation pass via free-radical creation as generated from the coating. The further addition of nanoscale (preferably less than 100 nm, particularly preferred less than 50 nm, and specifically preferred less than 10 nm) semi-conductive powders, including alumina or titania, increases the mean free path of free radicals generated. The further addition of conductive additive powder (also of nanoscale and preferably less than 100 nm, particularly preferred less than 50 nm, and specifically preferred less than 10 nm) within the substrate/coating polymer enhances the electron transport to the pathogen/microorganism to shorten the inactivation time by at least 5% (and preferably by at least 50%, and particularly preferred by at least 90%).

Figure 11:
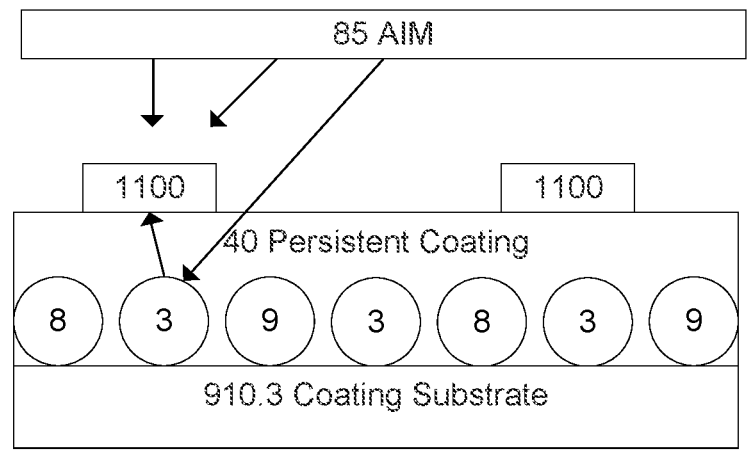
FIG. 11 is a side view depicting a multi-modal DRS including the multi-layer details of the persistent coating when the AIM is notably an optical emitter to generate free radicals from actives within the persistent coating.

Turning to FIG. 11, FIG. 11 depicts the use of AIM 85 (notably UV-C, or even visible light when the photocatalyst 3 is capable of the extended wavelength as known in the art) such that the emitted energy field both directly inactivates the pathogen(s) on the persistent coating 40 which has the embedded additives ranging from photocatalyst 3, semi-conductive powders 8 including TiO2 as well as functionalized TiO2, or additional ROS generating 9 additives that leverage the persistent coating to increase the yield of free radicals generated by way of additional ROS generated as a result of AIM 85 emitted energy interactions with the persistent coating 40. The vectors, which are just representative and understood to be virtually any direction, show that the AIM 85 emitted field impacts any surface pathogens 1100 (or even organics such as dust or dirt or toxic chemicals) directly but importantly also through the additive interaction (3, 8, 9) "reflecting" or "emitting" additional ROS.

Turning to FIG. 12, FIG. 12 depicts a top view (i.e., directly looking at the screen display) embodiment of DRS on a GUI touchscreen. The touch surface 10 as in the other embodiments is comprised of multiple touch segments (1.1, 1.2, 1.3, 1.4, 1.5, 1.51, 1.6, and 1.61) however these touch segments are fundamentally more reconfigurable as they are solely dictated by software placement. The principle of maximizing running time intervals between a first person's first user session and a second person's second user session remains the control system directive, though now having a much larger degree of flexibility. The implementation by the DRS distributed control system 695 or server 4000 notably through at least the GUI engine 3205 and touch location engine 3210.2, and preferably with the user profile engine 3211 (as shown in FIG. 4) coordinates the placement (via software and graphics display) of touch segments' placement on the touch surface 10 on the operational device to time interval between subsequent user sessions. The simplest embodiment is an alternating GUI placement of touch segments, whether that alternating placement is between two different sets of placements, three different sets of placements, or more to maximize time between subsequent touches by the different users. One such exemplary of this is the movement of touch segment 1.1 and 1.3 in a first scenario to the active touch segments respectively of 1.2 and 1.4. Another exemplary is the utilization of one set of touch segments (1.1 and 1.3) in the first portion of every user session followed by a different set of touch segments (1.2 and 1.4) in the second portion of every user session. Another exemplary is the DRS offsets the touch segments such as by utilizing touch segment 1.5 first for first user session and touch segment 1.51 for second user session such that the offset in at least one dimension or both (X, Y, or X and Y) is sufficient to ensure physical touch interactions in the first session do not occur in the same X,Y two dimensional space in the first user session as the second user session. All things equal, as the GUI is smaller in total dimension it becomes harder to ensure touch interactions in the first session are not utilized again in the second session. In such an instance, the DRS additionally uses the user profile engine 3211 to establish a probability that minimizes the likelihood of using the same touch segment in immediately subsequent user sessions. It is further understood that the DRS is likely to use offsets when the user sessions are very frequently used by the same person (i.e., a machine operator that enters a manufacturing order number multiple times a day or even week) and therefore that same person strongly desires repeatability to minimize the time and effort to interact with the GUI in which case the relative position of touch segments is best to remain relatively the same but an offset accomplishes the maximizing time interval between user sessions on the same touch segments resulting in only a slight recalibration (unconscious most likely) of starting X,Y position at the beginning of the session and not repeated recalibrations.

Although the invention has been described in detail, regarding certain embodiments detailed herein, other anticipated embodiments can achieve the same results. Variations and modifications of the present invention will be obvious to those skilled in the art and the present invention is intended to cover in the appended claims all such modifications and equivalents.

What is claimed is:

1. A dynamic cross-contamination reduction control system comprised of an operational device having an at least one touch surface whereby the at least one touch surface is interacted by physical touch by a first person in a first user session and then subsequently by a second person in a second user session; an at least one pathogen inactivation component to decontaminate the at least one touch surface; a microprocessor controller having an at least one sensor to monitor a last touch by the first person, a first touch by the second person, a running time touch interval between a current time and the time of the last touch by the first person, a starting time of the at least one pathogen inactivation component, a running inactivation process time from the current time and the starting time of the at least one pathogen inactivation component on the at least one touch surface, a pathogen inactivation effectiveness function whereby the pathogen inactivation effectiveness function is a function of at least one of a duration of time, a pathogen type, and a process intensity level; and a visual indicator that signals to the second person as calculated by the microprocessor controller a pathogen inactivation level on a real-time basis.

2. The dynamic cross-contamination reduction control system according to claim 1 whereby the at least one touch surface is comprised of an at least two touch segments, whereby the microprocessor monitors the running time touch interval for each of the at least two touch segments, whereby the visual indicator signals to the second person a first segment of the at least two touch segments having a higher pathogen inactivation effectiveness function on a real-time basis, and whereby a second segment of the at least two touch segments has a lower pathogen inactivation effectiveness function on a real-time basis.

3. The dynamic cross-contamination reduction control system according to claim 2 whereby the at least one touch surface is comprised of an at least two touch segments, wherein the at least one touch surface is a graphical user interface, whereby the microprocessor monitors the running time touch interval for each of the at least two touch segments, whereby the visual indicator is in a first position for the first user and in a second position for the second person whereby the microprocessor reconfigures the visual indicator from the first position to the second position when the first person touches the touch surface within the first position during the first user session such that the second user during the second user session doesn't touch the first position.

4. The dynamic cross-contamination reduction control system according to claim 2 whereby the at least one touch surface is comprised of an at least two touch segments, wherein the at least one touch surface is a graphical user interface, whereby the microprocessor controller monitors the running time touch interval for each of the at least two touch segments, whereby the visual indicator is in a first position for the first user and in a second position for the second person, whereby the microprocessor reconfigures the visual indicator from the first position to the second position when the first person touches the touch surface within the first position during the first user session such that the second user during the second user session will not touch the first position due to the microprocessor controller reconfiguration of the graphical user interface inactivates the first position as an active at least one touch surface during the second session, and whereby the microprocessor actuates an active pathogen inactivation method over the first position after an end of the first user session.

5. The dynamic cross-contamination reduction control system according to claim 2 whereby the at least one touch surface is comprised of an at least two touch segments, whereby the microprocessor controller monitors the running time touch interval for each of the at least two touch segments, whereby the at least one pathogen inactivation component to decontaminate the at least one touch surface is comprised of a persistent coating have efficacy to inactivate an at least one pathogen and an active pathogen inactivation component have efficacy to inactivate the at least one pathogen.

6. The dynamic cross-contamination reduction control system according to claim 5, whereby the microprocessor controller has a probability index of time between the first user session and the second user session, whereby the microprocessor actuates the active pathogen inactivation process when the probability index of time between the first user session and the second user session is less than the a time of the active pathogen inactivation component to reach the pathogen inactivation effectiveness function to reach a pathogen reduction threshold level.

7. The dynamic cross-contamination reduction control system according to claim 2 whereby a second visual indicator signals to the second person the second segment, and whereby the second person makes an active decision to avoid the second segment in favor of the first segment.

8. The dynamic cross-contamination reduction control system according to claim 2 whereby the at least one sensor to monitor a last touch by the first person is a motion sensor having an at least two motion sensitive areas to differentiate when the first person is leaving the operational device and the second person is approaching the operational device.

9. The dynamic cross-contamination reduction control system according to claim 2 further comprising an actuator to move the first segment from a first position to a second position and the second segment from the second position to the first position, an active pathogen inactivation component and a shield whereby the shield is in between the first position and the second position to protect the second person from the active pathogen inactivation component.

10. The dynamic cross-contamination reduction control system according to claim 1 whereby the at least one touch surface has a first touch segment and a second touch segment, whereby the first touch segment has an in-plane thermal barrier in thermal communication with the second touch segment, and whereby the thermal barrier reduces heat transfer between the first touch segment and the second touch segment by greater than 50% in comparison to the heat transfer between the first touch segment and the second touch segment when void of the in-plane thermal barrier in between the first touch segment and the second touch segment.

11. The dynamic cross-contamination reduction control system according to claim 1 whereby the at least one pathogen inactivation component to decontaminate the at least one touch surface is a thermal inactivation component, whereby the thermal inactivation component has a through-plane thermal barrier in thermal communication with both an air or water interface of the operational device and a coating substrate below the at least one touch surface, and whereby the through-plane thermal barrier reduces heat transfer between the thermal inactivation component and the coated substrate by greater than 50% in comparison to the heat transfer between the thermal inactivation component and the coated substrate when void of the through-plane thermal barrier in thermal inactivation component and the coating substrate.

12. The dynamic cross-contamination reduction control system according to claim 11 whereby the thermal inactivation component is comprised of a planar conductivity additive in a persistent coating, whereby the planar conductivity additive is within a bulk portion of the persistent coating, and whereby a non-planar conductivity additive is on the persistent coating in an array pattern whereby the array pattern creates a continuous conductivity circuit.

13. The dynamic cross-contamination reduction control system according to claim 12 whereby the non-planar thermal additive is a laser induced graphene.

14. A dynamic cross-contamination reduction control system comprised of an operational device having an intermediary non-stationary touch surface whereby the intermediary non-stationary touch surface has a physical touch interaction with a first stationary touch surface and then a second stationary touch surface, an at least one pathogen inactivation component to decontaminate the intermediary non-stationary touch surface after the physical touch interaction of the first stationary touch surface and before the physical touch interaction with the second stationary touch surface; a microprocessor controller having an at least one sensor to monitor the physical touch interaction with the first stationary touch surface, another physical touch interaction with the second stationary touch surface, a running time touch interval between a current time and the time of the physical touch interaction on the first stationary touch surface, a starting time of the at least one pathogen inactivation component, a running inactivation process time from the current time and the starting time of the at least one pathogen inactivation component on the first stationary touch surface, a pathogen inactivation effectiveness function whereby the pathogen inactivation effectiveness function is a function of at least one of a duration of time, a pathogen type, and a process intensity level; and a visual indicator that signals on the operational device as calculated by the microprocessor controller a pathogen inactivation level on a real-time basis.

15. The dynamic cross-contamination reduction control system according to claim 14 whereby the intermediary non-stationary touch surface has an in-plane thermal barrier in thermal communication with the at least one pathogen inactivation component, and whereby the thermal barrier reduces heat transfer between the operational device and the at least one pathogen inactivation component by greater than 50% in comparison to the heat transfer between the operational device and the at least one pathogen inactivation component when void of the in-plane thermal barrier in between the operational device and the at least one pathogen inactivation component.

16. The dynamic cross-contamination reduction control system according to claim 1 whereby the at least one pathogen inactivation component to decontaminate the at least one touch surface is a thermal inactivation component, whereby the thermal inactivation component has a through-plane thermal barrier in thermal communication with both an air or water interface of the operational device and a coating substrate below the intermediary non-stationary touch surface, and whereby the through-plane thermal barrier reduces heat transfer between the operational device and the intermediary non-stationary touch surface by greater than 50% in comparison to the heat transfer between the thermal inactivation component and the operational device when void of the through-plane thermal barrier in thermal inactivation component and the operational device.

17. The dynamic cross-contamination reduction control system according to claim 12 whereby the thermal inactivation component is comprised of a planar conductivity additive in a persistent coating, whereby the planar conductivity additive is within a bulk portion of the intermediary non-stationary touch surface, and whereby a non-planar conductivity additive is on the intermediary non-stationary touch surface in an array pattern whereby the array pattern creates a continuous conductivity circuit.

18. The dynamic cross-contamination reduction control system according to claim 12 whereby the non-planar thermal additive is a laser induced graphene.

19. A dynamic cross-contamination reduction control system comprised of an operational device having an at least one touch surface on a graphical user interface whereby the at least one touch surface is interacted by physical touch by a first person in a first user session on a first touch segment at a first position and then subsequently by a second person in a second user session on a second touch segment at a second position; an at least one pathogen inactivation component to decontaminate the at least one touch surface; a microprocessor controller having an at least one sensor to monitor a last touch by the first person, a first touch by the second person, a running time touch interval between a current time and the time of the last touch by the first person, a starting time of the at least one pathogen inactivation component, a running inactivation process time from the current time and the starting time of the at least one pathogen inactivation component on the at least one touch surface, a pathogen inactivation effectiveness function whereby the pathogen inactivation effectiveness function is a function of at least one of a duration of time, a pathogen type, and a process intensity level; and the microprocessor controller moves the first touch segment to a second touch segment on a real-time basis in between the first user session and the second user session.

20. The dynamic cross-contamination reduction control system according to claim 19 whereby the at least one pathogen inactivation component is comprised of a planar conductivity additive in a persistent coating, whereby the planar conductivity additive is within a bulk portion of the intermediary non-stationary touch surface, and whereby a non-planar conductivity additive is on the intermediary non-stationary touch surface in an array pattern whereby the array pattern creates a continuous conductivity circuit.

* * * * *